US012558006B2

(12) United States Patent
Hatch et al.

(10) Patent No.: US 12,558,006 B2
(45) Date of Patent: Feb. 24, 2026

(54) DEVICES, METHODS, AND SYSTEMS TO COLLECT, CONCENTRATE, STORE, AND ANALYZE CHEMICAL SUBSTANCES

(71) Applicant: SENSILL, INC., San Diego, CA (US)

(72) Inventors: Richard Hatch, Pleasanton, CA (US); Mitchell Levinson, Pleasanton, CA (US); Ardeshir Bayat, Malibu, CA (US); William Shea, Martinez, CA (US)

(73) Assignee: SENSILL, INC., Concord, CA (US)

( * ) Notice: Subject to any disclaimer, the term of this patent is extended or adjusted under 35 U.S.C. 154(b) by 306 days.

(21) Appl. No.: 18/129,720

(22) Filed: Mar. 31, 2023

(65) Prior Publication Data

US 2023/0243860 A1 Aug. 3, 2023

Related U.S. Application Data

(63) Continuation of application No. PCT/US2021/064142, filed on Dec. 17, 2021, which
(Continued)

(51) Int. Cl.
*A61B 5/145* (2006.01)
*A61B 5/00* (2006.01)
(Continued)

(52) U.S. Cl.
CPC ...... *A61B 5/14546* (2013.01); *A61B 5/14507* (2013.01); *A61B 5/1477* (2013.01);
(Continued)

(58) Field of Classification Search
CPC ........... A61B 5/14546; A61B 5/14507; A61B 5/1477; A61B 5/6831; A61B 5/6832;
(Continued)

(56) References Cited

U.S. PATENT DOCUMENTS

| | | | | |
|---|---|---|---|---|
| 1,061,206 A | | 5/1913 | Tesla | |
| 2,714,308 A | * | 8/1955 | Heck | E21B 21/067 |
| | | | | 73/152.04 |

(Continued)

FOREIGN PATENT DOCUMENTS

| | | | |
|---|---|---|---|
| CN | 108786375 A | | 11/2018 |
| CN | 109233899 | * | 1/2019 |

(Continued)

OTHER PUBLICATIONS

Ashrafi et al., "A Microbiome and Metabolomic Signature of Phases of Cutaneous Healing Identified by Profiling Sequential Acute Wounds of Human Skin: An Exploratory Study," PLOS One, 26 pages, Feb. 26, 2020.

(Continued)

*Primary Examiner* — Robert R Raevis

(74) *Attorney, Agent, or Firm* — Seager, Tufte & Wickhem LLP

(57) ABSTRACT

Concentrating devices, systems, and methods include those for separating fluids to be sensed (e.g., analytes, such as volatile organic compounds (VOCs) and/or other chemical substances) from other fluid (e.g., a carrier gas, air, etc.) of a fluid mixture received from a target area of a subject's anatomy (e.g., a subject's skin, a wound on a subject, etc.). In some cases, the concentration system may include a housing and a rotor positioned in a compartment of the housing. The housing may receive a fluid mixture in the compartment and rotation of the rotor relative to the housing may separate fluid to be sensed in the fluid mixture from other fluid of the fluid mixture.

14 Claims, 12 Drawing Sheets

Related U.S. Application Data is a continuation-in-part of application No. PCT/US2021/058272, filed on Nov. 5, 2021, and a continuation-in-part of application No. PCT/US2021/053167, filed on Oct. 1, 2021.

(60) Provisional application No. 63/128,048, filed on Dec. 19, 2020, provisional application No. 63/128,050, filed on Dec. 19, 2020, provisional application No. 63/114,734, filed on Nov. 17, 2020, provisional application No. 63/111,077, filed on Nov. 8, 2020, provisional application No. 63/087,128, filed on Oct. 2, 2020.

(51) Int. Cl.

| | |
|---|---|
| *A61B 5/1477* | (2006.01) |
| *A61B 10/00* | (2006.01) |
| *G01N 21/78* | (2006.01) |
| *G01N 35/04* | (2006.01) |
| *G01N 35/10* | (2006.01) |
| *G01N 35/00* | (2006.01) |

(52) U.S. Cl.
CPC .......... *A61B 5/6831* (2013.01); *A61B 5/6832* (2013.01); *A61B 10/0045* (2013.01); *G01N 21/78* (2013.01); *G01N 35/04* (2013.01); *G01N 35/1009* (2013.01); *A61B 5/445* (2013.01); *A61B 2562/046* (2013.01); *A61B 2562/164* (2013.01); *A61B 2562/168* (2013.01); *G01N 2035/00306* (2013.01); *G01N 2035/0429* (2013.01); *G01N 2035/0441* (2013.01)

(58) Field of Classification Search
CPC .............. A61B 10/0045; A61B 5/445; A61B 2562/046; A61B 2562/164; A61B 2562/168; A61B 10/0064; A61B 2010/0083; A61B 2010/0067; G01N 21/78; G01N 35/04; G01N 35/1009; G01N 2035/00306; G01N 2035/0429; G01N 2035/0441; A61F 13/00051; B01D 17/0217; B01D 19/0057; B01D 45/12; B01D 45/14; B01D 53/24
USPC ............ 73/1.02, 31.07, 863.21; 96/167, 177, 96/195, 196, 208, 213, 214, 216, 217; 95/34, 35, 219, 270
See application file for complete search history.

(56) References Cited

U.S. PATENT DOCUMENTS

| | | | | |
|---|---|---|---|---|
| 4,225,324 A | * | 9/1980 | Gazda | B04B 5/08 |
| | | | | 494/900 |
| 5,512,083 A | | 4/1996 | Dunne | |
| 5,970,803 A | | 10/1999 | Staples et al. | |
| 6,063,041 A | | 5/2000 | Flament et al. | |
| 6,251,083 B1 | | 6/2001 | Yum et al. | |
| 6,368,558 B1 | | 4/2002 | Suslick et al. | |
| 6,495,102 B1 | | 12/2002 | Suslick et al. | |
| 6,716,269 B1 | * | 4/2004 | Graff | B04B 9/06 |
| | | | | 95/35 |
| 7,261,857 B2 | | 8/2007 | Suslick et al. | |
| 7,967,893 B2 | | 6/2011 | Schroeder | |
| 8,597,414 B2 | * | 12/2013 | Bloom | B04B 5/08 |
| | | | | 55/315 |
| 8,852,504 B2 | | 10/2014 | Suslick et al. | |
| 9,249,446 B2 | | 2/2016 | Suslick et al. | |
| 9,856,446 B2 | | 1/2018 | Suslick et al. | |
| 9,880,137 B2 | | 1/2018 | Lim et al. | |
| 10,539,508 B2 | | 1/2020 | Suslick et al. | |
| 10,575,780 B2 | | 3/2020 | Van Den Ende et al. | |
| 11,035,800 B2 | | 6/2021 | Suslick et al. | |
| 2005/0155493 A1 | * | 7/2005 | Dean | B01D 19/0052 |
| | | | | 96/214 |
| 2006/0230933 A1 | * | 10/2006 | Harazim | B01D 53/24 |
| | | | | 95/270 |
| 2010/0313751 A1 | * | 12/2010 | Hassan | B04B 5/08 |
| | | | | 95/35 |
| 2011/0209613 A1 | | 9/2011 | Jensen et al. | |
| 2012/0074073 A1 | | 3/2012 | Coull et al. | |
| 2012/0283529 A1 | | 11/2012 | Marchand et al. | |
| 2013/0025455 A1 | * | 1/2013 | Morrison | B01D 53/24 |
| | | | | 95/271 |
| 2015/0359469 A1 | | 12/2015 | Jacobs et al. | |
| 2018/0031486 A1 | | 2/2018 | Myyrylinen et al. | |
| 2019/0217307 A1 | | 7/2019 | Umeda | |
| 2021/0356307 A1 | * | 11/2021 | Gysling | G01F 1/8436 |

FOREIGN PATENT DOCUMENTS

| | | | | |
|---|---|---|---|---|
| EP | 3085449 | * | 10/2016 | |
| JP | 2018504171 A | | 2/2018 | |
| WO | 2005/030361 | * | 4/2005 | |
| WO | 2016096391 A | | 6/2016 | |
| WO | 2017037569 A1 | | 3/2017 | |
| WO | 2019135232 A1 | | 7/2019 | |

OTHER PUBLICATIONS

Ashrafi et al., "Validation of Biofilm Formation on Human Skin Wound Models and Demonstration of Clinically Translatable Bacteria-Specific Volatile Signatures," Scientific Reports, vol. 8, No. 9431, pp. 1-16, 2018.

Craven et al., "The Fluid Dynamics of Canine Olfaction: Unique Nasal Airflow Patterns as an Explanation of Macrosmia," J.R. Soc. Interface, pp. 933-943, 2009.

Daulton et al., The Detection of Wound Infection by Ion Mobility Chemical Analysis, Biosensors, vol. 120, No. 19, pp. 1-9.

Dries "Management of Burn Injuries—Recent Developments in Resucitation, Infection Control and Outcomes Research," Scandanavian Journal of Trauma, Resucitation and Emergency Medicine, vol. 7, No. 14, 13 pages, 2009.

Edelsberg et al., "Trends in US Hospital Admissions for Skin and Soft Tissue Infections," Emerging Infectious Diseases, vol. 15, No. 9, pp. 1516-1518, Sep. 2009.

Jiang et al., "A Non-Invasive Method for In Vivo Skin Volatile Compounds Sampling," Analytica Chimica Acta, vol. 804, pp. 111-119, 2013.

Lagasse et al., "Colorimetric Sensor Arrays: Development and Application to Art Conservation," Journal of the American Conservation, vol. 47, No. 3, pp. 127-140, 2018.

Li et al., "Ultrasensitive Monitoring of Museum Airborne Pollutants Using a Silver Nanoparticle Sensor Array," American Chemical Society, vol. 5, pp. 2783-2791, 2020.

Nussbaum et al. "An Economic Evaluation of the Impact, Cost, and Medicare Policy Implications of Chronic Nonhealing Wounds," Value in Health, vol. 21, pp. 27-32, 2018.

Sekine et al., Determination of Acetaldehyde and Acetone Emanating from Human Skin using a Passive Flux Sampler—HPLC System, Journal of Chromatography B, vol. 859, pp. 201-207, 2007.

Sen et al., "Human Skin Wounds: A Major and Snowballing Threat to Public Health and the Economy," Wound Repair Regeneration, vol. 17, No. 6, pp. 763-771, 2009.

Sen "Human Wounds and Its Burden: An Updated Compendium of Estimates," (Editorial), Advances in Wound Care, vol. 8, No. 2, pp. 39-48, 2019.

Thomas et al., "Novel Noninvasive Identification of Biomarkers by Analytical Profiling of Chronic Wounds using Volatile Organic Compounds," Wound Repair and Regeneration, vol. 18, Issue 4, pp. 391-400, 2010. (Abstract).

Zi et al., "Chemically Induced Sintering of Nanoparticles," Angewandte Chemie, vol. 131, pp. 14331-14334, 2019.

(56) References Cited

OTHER PUBLICATIONS

Ashrafi et al., "Volatile Organic Compound Detection as a Potential Means of Diagnosing Cutaneous Wound Infections," Wound Repair and Regeneration, vol. 25, Issue 4, pp. 574-590, 2017. Accessed Jul. 18, 2023. (Abstract).

International Search Report and Written Opinion for International Application No. PCT/US2021/053167 mailing date Jan. 24, 2022, 13 pages.

International Search Report and Written Opinion for International Application No. PCT/US2021/058272 mailing date , Feb. 28, 2022. 11 pages.

* cited by examiner

1

DEVICES, METHODS, AND SYSTEMS TO COLLECT, CONCENTRATE, STORE, AND ANALYZE CHEMICAL SUBSTANCES

CROSS-REFERENCE TO RELATED APPLICATIONS

This application is a continuation of International Application No. PCT/US2021/064142, filed on Dec. 17, 2021, which claims priority to U.S. Provisional Application Ser. No. 63/128,048, filed Dec. 19, 2020, the entirety of which is incorporated herein by reference and U.S. Provisional Application Ser. No. 63/128,050, filed Dec. 19, 2020, the entirety of which is incorporated herein by reference. This application is a continuation-in-part of PCT Patent Application No. PCT/US2021/058272, filed Nov. 5, 2021, the entirety of which is incorporated herein by reference. This application is a continuation-in-part of PCT/US2021/053167, filed Oct. 1, 2021, the entirety of which is incorporated herein by reference, which claims priority to U.S. Provisional Application Ser. No. 63/114,734, filed Nov. 17, 2020, the entirety of which is incorporated herein by reference, U.S. Provisional Patent Application No. 63/111,077, filed Nov. 8, 2020, the entirety of which is incorporated herein by reference, and U.S. Provisional Patent Application No. 63/087, 128, filed Oct. 2, 2020, the entirety of which is incorporated herein by reference.

TECHNICAL FIELD

The present disclosure pertains to collection, concentration, storage, and analysis tools, and the like. More particularly, the present disclosure pertains to devices and systems for collecting, concentrating, storing, and analyzing chemical substances, and methods for manufacturing and using such devices.

BACKGROUND

A wide variety of medical devices have been developed in the medical field for collection, storing, and analysis of samples. These devices are manufactured by any one of a variety of different manufacturing methods and may be used according to any one of a variety of methods. Of the known medical devices and methods, each has certain advantages and disadvantages.

BRIEF SUMMARY

This disclosure provides design, material, manufacturing method, and use alternatives for medical devices. Although it is noted that collection, storing and analysis approaches and systems are known, there exists a need for improvement on those approaches and systems.

An example fluid concentrator may include a housing defining a compartment, an inlet to the compartment, and an outlet from the compartment, and a rotor positioned in the compartment and configured to rotate relative to the housing. The housing may be configured to receive through the inlet and into the compartment a fluid mixture including a fluid to be sensed and rotation of the rotor relative to the housing separates the fluid to be sensed from other fluid of the fluid mixture.

Alternatively or additionally to any of the embodiments in this section, rotation of the rotor relative to the housing may cause the fluid to be sensed to exit the compartment through the outlet.

Alternatively or additionally to any of the embodiments in this section, the fluid mixture may enter the compartment at a radial location closer to a rotational axis of the rotor than a radial location at which the fluid to be sensed exits the compartment, and the rotation of the rotor causes the fluid to be sensed to move radially outward from the rotational axis to the radial location at which the fluid to be sensed exits the compartment.

Alternatively or additionally to any of the embodiments in this section, the fluid to be sensed may include volatile organic compounds (VOCs) from a mammalian subject.

Alternatively or additionally to any of the embodiments in this section, the fluid concentrator may further include a bearing system and the bearing system may be configured to facilitate rotation of the rotor relative to the housing.

Alternatively or additionally to any of the embodiments in this section, the bearing system may be a magnetic bearing system.

Alternatively or additionally to any of the embodiments in this section, the rotor may comprise a disc.

Alternatively or additionally to any of the embodiments in this section, the outlet may be a first outlet and the housing may define a second outlet, the second outlet is positioned closer to a rotational axis of the rotor than the first outlet.

Alternatively or additionally to any of the embodiments in this section, the rotor may comprise one or more holes extending through the rotor from a first side of the rotor to a second side of the rotor and fluid passing through the one or more holes is configured to exit through the second outlet.

Alternatively or additionally to any of the embodiments in this section, the rotor may include one or more slots extending radially outward and through the rotor from a first side of the rotor to a second side of the rotor and the fluid to be sensed passing through the one or more slots is configured to exit through first outlet.

Alternatively or additionally to any of the embodiments in this section, the rotor may comprise a first rotator cover covering at least a portion of the first side of the rotor and at least part of the one or more slots, the first rotator cover defining an inlet port for the fluid mixture to the one or more slots, a second rotator cover covering at least a portion of the second side of the rotor and at least part of the one or more slots, the second rotator cover defining a first outlet port from the one or more slots and a second outlet port from the one or more slots that is spaced radially inward from the first outlet port, and the first outlet may be configured to be in fluid communication with the first outlet and the second outlet port is configured to be in fluid communication with the second outlet.

Alternatively or additionally to any of the embodiments in this section, the fluid concentrator may further include a plurality of rotors positioned in the compartment and configured to rotate relative to the housing.

Alternatively or additionally to any of the embodiments in this section, each rotor of the plurality of rotors may comprise one or more holes extending through the rotor from a first side of the rotor to a second side of the rotor.

Alternatively or additionally to any of the embodiments in this section, the fluid concentrator may further include a detector array in fluid communication with the compartment and configured to detect one or more parameters of the fluid to be sensed.

Alternatively or additionally to any of the embodiments in this section, the detector array is located in the compartment.

In a further example, a fluid concentration system may comprise a fluid concentrator comprising a housing defining a compartment, an inlet to the compartment, and an outlet from the compartment, a rotor positioned in the compartment and configured to rotate relative to the housing, and wherein rotation of the rotor relative to the housing is configured to cause a fluid mixture received in the compartment to rotate and a fluid to be sensed of the fluid mixture to move toward the outlet, and a fluid path in communication with the outlet configured to transport the fluid to be sensed from the outlet.

Alternatively or additionally to any of the embodiments in this section, the fluid concentration system may include a detector in communication with the fluid path and the detector may be configured to detect one or more parameters of the fluid to be sensed.

Alternatively or additionally to any of the embodiments in this section, the fluid concentration system may include a collector in communication with the fluid path, and the collector may be configured to adsorb the fluid to be sensed.

Alternatively or additionally to any of the embodiments in this section, the fluid concentration system may include a plurality of fluid concentrators, each of the plurality of fluid concentrators may comprise a housing defining a compartment, an inlet to the compartment, and an outlet from the compartment, a rotor positioned in the compartment and configured to rotate relative to the housing, and rotation of the rotor relative to the housing may be configured to cause a fluid mixture received in the compartment to rotate and a fluid to be sensed of the fluid mixture to move toward the outlet, each of the plurality of fluid concentrators of the plurality of fluid concentrators is in fluid communication with at least one other of the plurality of fluid concentrators.

Alternatively or additionally to any of the embodiments in this section, the fluid concentration system may include a plurality of fluid paths, a first fluid concentrator of the plurality of fluid concentrators may receive the fluid mixture through the inlet of the first fluid concentrator, and a fluid path of the plurality of fluid paths may be fluidly coupled the outlet of one of the plurality of fluid concentrators to the inlet of another of the plurality of fluid concentrators.

Alternatively or additionally to any of the embodiments in this section, for two or more of the plurality of fluid concentrators, the outlet may be a first outlet and the housing defines a second outlet, the second outlet is positioned closer to a rotational axis of the rotor than the first outlet, the first outlet of a first fluid concentrator of the plurality of fluid concentrators is fluidly coupled to a first outlet of one or more of the plurality of fluid concentrators, and the second outlet of the first fluid concentrator is fluidly coupled to an inlet of a second fluid concentrator of the plurality of fluid concentrators.

Alternatively or additionally to any of the embodiments in this section, a fluid concentrator of the plurality of fluid concentrators may include a detector in fluid communication with the housing, the detector may be configured to detect one or more parameters of the fluid to be sensed.

Alternatively or additionally to any of the embodiments in this section, the fluid concentration system may include a pump configured to pump fluid mixture to the inlet.

In a further example, a method may comprise receiving a mixture of fluid at a fluid concentrator, separating fluid to be sensed from other fluid of the mixture of fluid, and outputting the separated fluid to be sensed from the fluid concentrator.

Alternatively or additionally to any of the embodiments in this section, separating fluid to be sensed from other fluid of the mixture of fluid may comprise rotating the mixture of fluid to cause the fluid to be sensed to move radially outward relative to the other fluid of the mixture of fluid.

Alternatively or additionally to any of the embodiments in this section, the method may further include outputting the other fluid of the mixture of fluid from the fluid concentrator.

Alternatively or additionally to any of the embodiments in this section, the other fluid of the mixture of fluid may be outputted from a first fluid concentrator to an inlet of a second fluid concentrator.

Alternatively or additionally to any of the embodiments in this section, the other fluid of the mixture of fluid is outputted from the fluid concentrator to a subject for mixing with volatile organic compounds (VOCs) from a subject's skin.

Alternatively or additionally to any of the embodiments in this section, the method may further include receiving the other fluid that has mixed with VOCs from a subject's skin at the fluid concentrator.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
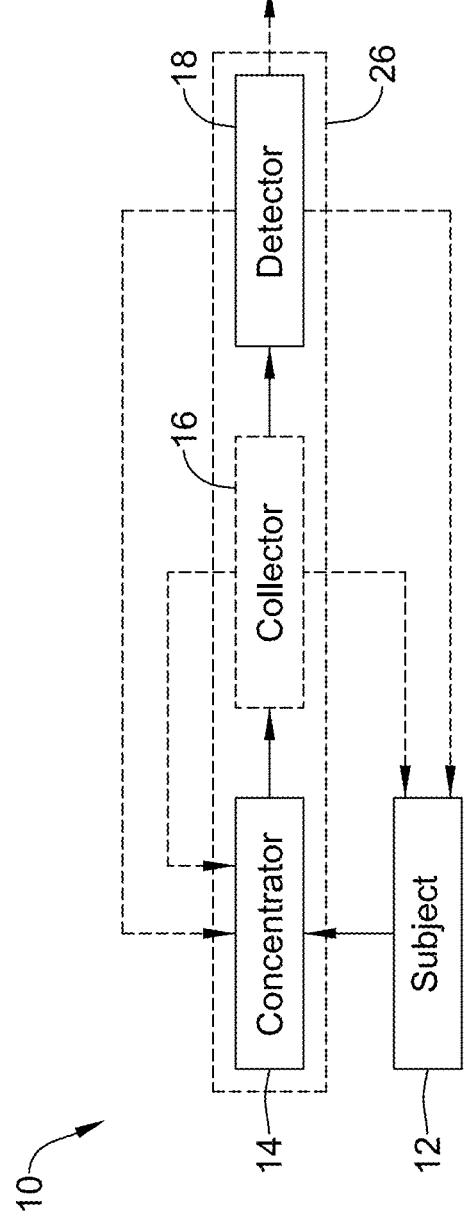
FIG. 1 is a schematic box diagram of an illustrative fluid concentration system.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure. The term "fluid" has the commonly accepted technical meaning, which includes liquids, gasses, and/or other suitable fluids.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used in connection with other embodiments whether or not explicitly described unless clearly stated to the contrary.

Chemical substances (e.g., analytes) migrate from inside a subject's body to an exterior surface of the subject's anatomy (e.g., a skin surface or other suitable surface) by diffusion across the epidermis from cutaneous capillaries, sweat glands (eccrine, and apocrine glands), and sebaceous glands. In addition, the epidermis of the skin continuously sheds thousands of cells into the environment, which are replaced by differentiating cells from the layer below. These dead cells transport body secretions, and importantly bacteria, which act on the dead cells and envelope them in a minute vapor cloud. Example substances emitted, excreted, emanated, released, and/or secreted from, to, or through the exterior surface of a subject's anatomy include, but are not limited to, sweat, water, minerals, natural compounds, xenobiotic compounds, sebum, protein degradation products, volatile organic compounds (VOCs), and/or other suitable substances emitted from, to, or through the skin surface. Through changes in metabolic profiles of chemical substances produced by the body, physiological and pathological information may be identified.

VOCs are chemical compounds containing carbon that have a high enough vapor pressure under normal conditions to significantly vaporize and enter the atmosphere. VOCs and other chemical substances are produced from sweat and sebum as well as and in addition to their interactions with resident skin or wound bacteria. VOCs are continuously being produced by a mammalian body's metabolism, including the metabolism of the human body, and released into the air predominantly via skin, breath, feces, and urine. Thus, VOCs can instantaneously reflect normal or abnormal physiological and pathological biochemical processes occurring in the body at a time of measurement.

A complex profile of VOCs and/or other chemical substances emanates from exterior surfaces of human anatomy (e.g., skin, wounds, etc.), which is altered by changes in the body's metabolic or hormonal state, the external environment, and the bacterial species colonizing at the exterior surfaces. Based on this, bacterial biofilm formation in human ex vivo cutaneous wound models and their specific VOC profiles have been developed. These models and profiles provide a vehicle for human skin-relevant biofilm studies and VOC detection that has potential clinical translatability in efficient non-invasive diagnosis of wound infection, as discussed in Validation Of Biofilm Formation On Human Skin Wound Models And Demonstration Of Clinically Translatable Bacteria-Specific Volatile Signatures, Ashrafi M, Novak Frazer L, Bates M, Baguneid M, Alonso-Rasgado T, Xia G, Rautemaa-Richardson R, Bayat A, Sci Rep. 2018 Jun. 21; 8(1): 9431, doi: 10.1038/s41598-018-27504-z), which is hereby incorporated by reference in its entirety for any and all purposes.

Capture and identification of VOCs and other chemical substances emanating from a target location of, on, or from a subject's anatomy (e.g., skin of a human body, wounds on the human body, feces or urine from the human body, exhalation from the human body, etc.) may be utilized for non-invasive, objective, and measurable monitoring and/or analysis of metabolic pathways, and can also illustrate how these pathways are altered over time and even respond to therapy in disease processes. For example, a change in a human body's metabolism equilibrium in response to a therapy can cause an alteration of VOCs and/or other chemical substances produced from the human body that is measurable and is indicative of how the human body is responding to the therapy. Further, collected VOCs and/or other chemical substances from a target location of or on a subject may result in determining a wellness of the subject (e.g., when collected VOCs and/or other chemical substances are compared to previously or future collected VOCs and/or other chemical substances, etc.)

In addition, microorganisms release VOCs and/or other chemical substances. The ability to identify these VOCs and/or other chemical substances from microorganisms in infected cutaneous wounds of a mammalian subject, such as a human being, results in efficient non-invasive diagnoses.

Diagnostic procedures utilizing VOCs and/or other chemical substances from a subject may be non-invasive and thus are an attractive alternative for patients compared to current invasive laboratory tests performed in hospitals and/or other medical settings, which take significant time and cannot provide instant point of care testing. In one example, use of VOCs to diagnose wound infections is discussed in Volatile Organic Compound Detection As A Potential Means Of Diagnosing Cutaneous Wound Infections, Ashrafi M, Bates M, Baguneid M, Alonso-Rasgado T, Rautemaa-Richardson R, Bayat A, Wound Repair Regen, 2017 August; 25(4): 574-590. doi: 10.1111/wrr.12563, Epub 2017 Aug. 31, which is hereby incorporated by reference in its entirety for any and all purposes.

Various devices and system may be utilized to collect and/or analyze VOCs and/or other chemical substances. Some devices used for collection of VOCs and/or other chemical substances are configured to collect VOC onto an adsorption pad. Example devices and techniques used for collection of VOC and/or other chemical substances are described in PCT Patent Application No. PCT/US21/53167, filed on Oct. 1, 2021, and titled DEVICES, METHODS, AND SYSTEMS TO COLLECT, STORE, AND ANALYZE CHEMICAL SUBSTANCES, which was previously incorporated by reference in its entirety for any and all purposes. Some devices used for collection of VOCs and/or other chemical substances from a subject are configured to detect VOCs using colorimetric sensor arrays and/or other suitable detectors. Example devices and techniques used for detecting VOCs and/or other chemical substances are described in PCT Patent Application No. PCT/US21/58272, filed on Nov. 5, 2021, and titled DEVICES, METHODS, AND SYSTEMS TO COLLECT, STORE, AND ANALYZE CHEMICAL SUBSTANCES, which was previously incorporated by reference in its entirety for any and all purposes.

In order to analyze VOCs and/or other chemical substances collected on an adsorption pad, additional steps of transporting the VOCs and/or other chemical substances to an analysis system or location and desorbing the collected VOCs and/or other chemical substances from the adsorption pad may be required, which take time and can add complexity to the collection and analysis of VOCs and/or other chemical substances from a subject. This process has the potential to contaminate the sample with other VOCs and/or chemical substances that may be present during this adsorption or desorption process.

Further, some devices or systems used for collection of VOCs and/or other chemical substances are configured to gather VOCs and/or other chemical substances by inhalation of air or other gasses mixed with VOCs and/or other chemical substances. Use of such devices or systems may result in obtaining a relative diluted mixture of gasses and VOCs and/or other chemical substances, which may increase the difficulty of collecting, detecting, and analyzing VOCs and/or other chemical substances that may be produced by a subject in relatively small volumes or concentrations. As such, the fluid mixture collected (e.g., VOCs and/or other chemical substances along with air and/or carrier fluid) may have a lower concentration of VOCs and/or other chemical substances (e.g., analyte) than desired for adequate detection, identification, and/or quantification. In some cases, VOCs and/or other chemical substances that are collected at a subject may need to be transported or moved to remote analysis locations, which has the potential to dilute and/or contaminate the collected VOCs and/or other chemical substances and adds to the complexity of the analysis and the length of time needed for the analysis of the collected VOCs and/or other chemical substances.

Further, where VOCs and/or other chemical substances are diluted into air or a carrier gas, it may be the case that the absolute concentration of VOCs and/or other chemical substances (e.g., a fluid to be sensed) a fluid mixture will be unknown. This can create a challenge for the analysis of the fluid to be sensed, especially when attempting to quantify VOCs and/or other chemical substances in an effort to measure or track the amount of bacteria in a wound or progression of other illness.

To capture a fluid that has a desired concentration level of a desired analyte, it may be desirable to separate the fluid to be sensed (e.g., the analyte) from the other fluid of the fluid mixture. As such, in some cases, a concentrator may be utilized along with a collector and/or detector of analyte from a subject to arrive at a more accurate analysis than if a concentrator were not utilized.

The disclosed concepts provide devices, systems, and methods that facilitate collection, increasing a concentration, and analysis of analytes (e.g., VOCs and/or other chemical substances, etc.) from a target location on an exterior surface of a subject that may or may not require additional gasses or liquids to collect and that may facilitate analysis of the VOCs and/or other chemical substances at or adjacent a collection site. In one example, the devices, systems, and methods that facilitate collection, concentration, and analysis of VOCs and/or other chemical substances may include a concentrator device that receives VOCs and/or other chemical substances from a subject in a mixed fluid and separates the VOCs and/or other chemical substances to be sensed or detected from other fluid of the mixed fluid. The VOCs and/or other chemical substances to be sensed or detected may be detected and/or sensed at the concentrator device and/or output to a further device for collection, detection, and/or analysis.

The use of a concentrator device may facilitate increasing a signal-to-noise ratio in detecting VOCs and/or other chemical substances by concentrating the VOCs and/or other chemical substances prior to passing them over or through a detector. In some cases, a centrifuge may be used as a concentrator to increase a concentration of VOCs and/or other chemical substances from a subject during and/or prior to detections of the VOCs and/or other chemical substances.

Additionally or alternatively to devices, systems, and methods that facilitate collection, concentration, and analysis of analytes from a target location on an exterior surface of a subject, the devices, systems, and methods described herein may be utilized to detect and/or analyze analytes from other suitable target locations of, on, or from the subject. For example, devices that facilitate collection, concentration, analysis, and/or detection of analytes from a target location may be configured to collect, concentrate, analyze, and/or detect analytes from exhalations (e.g., breath), urine, feces, throat cultures, wound cultures, and/or other suitable target locations of, on, and/or from the subject.

Turning to the Figures, FIG. 1 depicts a schematic view of an illustrative fluid concentration system 10 configured to concentrate VOCs and/or other chemical substances from a subject 12 (e.g., a mammalian body, such as a human body, or other suitable animal patient or subject). The fluid concentration system 10 may include a concentrator 14 (e.g., a fluid concentrator), a collector 16, a detector 18, and/or one or more other suitable components. The concentrator 14 may be configured to receive a fluid mixture from the subject 12 and concentrate VOCs and/or other chemical substances from the subject 12 for collection by the collector 16 and/or detection by the detector 18. Though other optional configurations are contemplated, the arrowed broken lines depicted in FIG. 1 represent optional configurations.

The collector 16 may be configured to collect VOCs and/or other suitable chemical substances from the subject 12. To facilitate collecting VOCs and/or other suitable chemical substances from the subject 12, the fluid passing through the collector 16 may be returned a target area of or adjacent the subject 12 and/or returned to the concentrator 14 for mixing with other fluid containing VOCs and/or other suitable chemical substances from the subject 12.

Although the collector 16 is depicted as being downstream of the concentrator 14, the collector 16 is represented in broken lines to demonstrate that it may be located at one or more other locations of the concentration system 10 (e.g., upstream of the concentrator 14 and/or other suitable locations). In some cases, the collector 16 may be entirely or at least partially incorporated into the concentrator 14. Further, the collector 16 may be omitted from the concentration system 10, as desired.

The collector 16 may be any suitable type of collector configured to collect VOCs and/or other chemical substances from a subject. Non-limiting examples of collectors 16 are described in PCT Patent Application No. PCT/US21/53167, filed on Oct. 1, 2021, and titled DEVICES, METH- ODS, AND SYSTEMS TO COLLECT, STORE, AND ANALYZE CHEMICAL SUBSTANCES, which was previously incorporated by reference herein in its entirety for any and all purposes.

The detector 18 may be configured to detect and/or sense analyte in fluid from the subject 12. To facilitate detecting and/or sensing analyte from the subject 12, the fluid passing through the detector 18 may be returned a target area of or adjacent the subject 12 and/or returned to the concentrator 14 for mixing with other fluid containing analyte from the subject 12.

Although the detector 18 is depicted as being downstream of the collector 16, the detector 18 may, alternatively or additionally, directly receive a concentrated fluid of analytes (e.g., VOCs and/or other chemical substances) from the concentrator 14. In some cases, the detector 18 may be entirely or at least partially incorporated into the concentrator 14. Further, the detector 18 may be omitted from the concentration system 10, as desired.

The detector 18 may be any suitable type of detector configured to detect and/or sense analytes from a subject. Non-limiting examples of detectors 18 are described in PCT Patent Application No. PCT/US21/58272, filed on Nov. 5, 2021, and titled DEVICES, METHODS, AND SYSTEMS TO COLLECT, STORE, AND ANALYZE CHEMICAL SUBSTANCES, which was previously incorporated by reference herein in its entirety for any and all purposes.

The concentrator 14, the collector 16, and the detector 18 may be configured in any suitable manner with respect to one another. In some cases, the concentrator 14, the collector 16, and/or the detector 18 may be configured to be fluidly coupled to one another while in proximity to one another. Although not required, two or more of the concentrator 14, the collector 16, and the detector 18 may be positioned in a housing 26 together.

Figure 2:
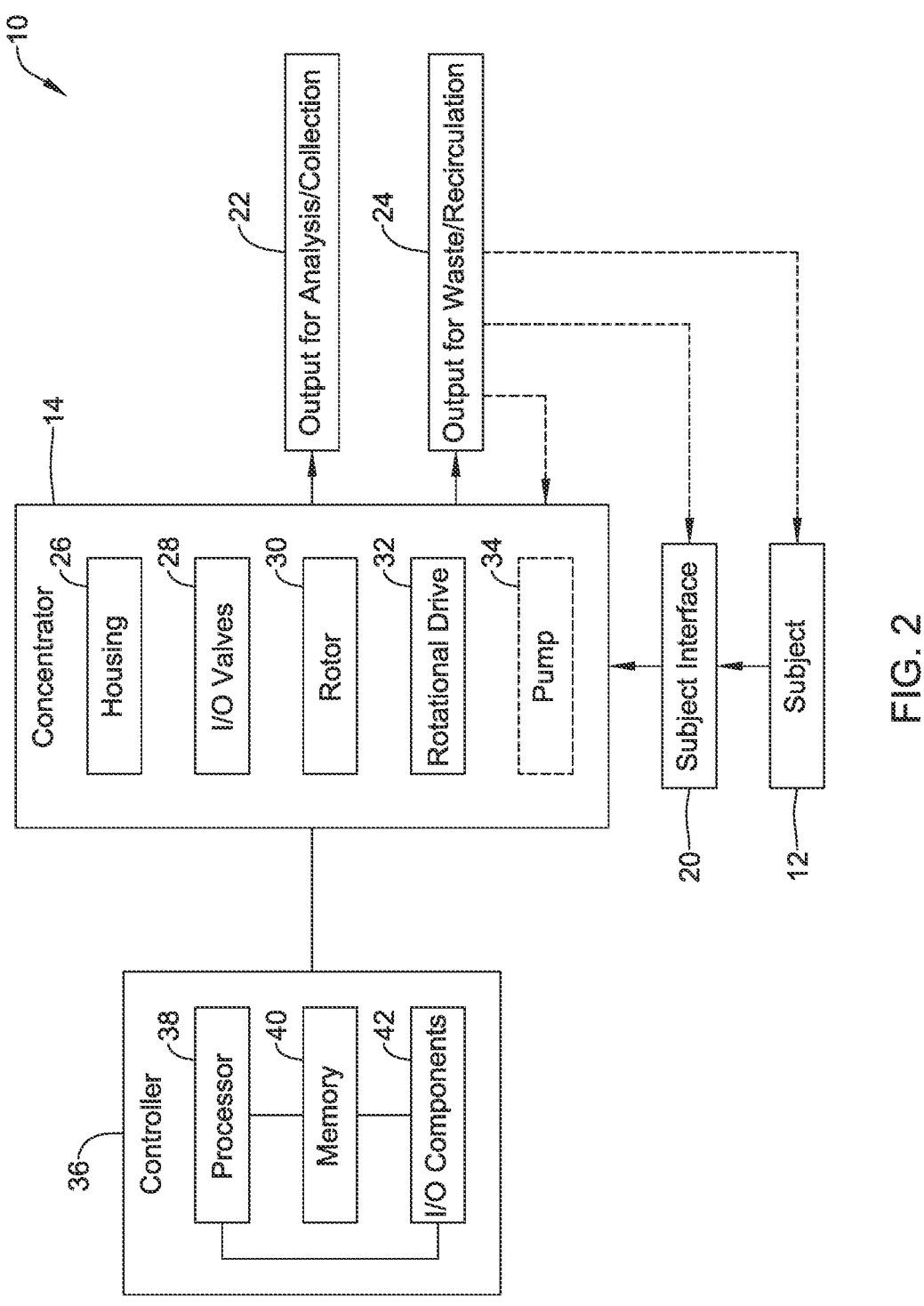
FIG. 2 is a schematic box diagram of an illustrative fluid concentration system.

FIG. 2 is a schematic illustration of the concentration system 10 configured to concentrate VOCs and/or other chemical substances from the subject 12 via a subject interface 20. The subject interface may be the collector 16, the detector 18, and/or other suitable component configured to interface with the subject 12 and the concentrator 14 by facilitation a fluid flow from the subject 12 to the concentrator 14. Although the concentration system 10 in FIG. 2 does not depict the collector 16 and the detector 18, the concentration system 10 may include and/or be configured to fluidly couple to the collector 16 and/or the detector 18.

The fluid concentrator 14 depicted in FIG. 2 may be configured to provide an output 22 for analysis and/or collection and an output 24 for waste and/or recirculation. The output 22 for analysis and/or collection may be an output of concentrated fluid of VOCs and/or other chemical substances (e.g., a fluid to be sensed) separated from other fluid of a fluid mixture received from the subject 12. The output 24 for waste and/or recirculation may be an output of the other fluid from the fluid mixture and may be exhausted, collected, analyzed, and/or recirculated to the subject 12, the concentrator 14, and/or the subject interface 20 (e.g., as represented by the arrowed broken lines).

The fluid concentrator 14 may include any suitable components. In one example, the fluid concentrator 14 may include the housing 26, I/O (input and/or output) valves 28, a rotor 30, a rotational drive 32, a pump 34, and/or one or more other suitable components. Further, the concentrator 14 may include and/or be in communication with one or more controllers 36.

The housing 26 may be any suitable type of housing configured to define a compartment. In some cases, the housing 26 may be formed from one or more components coupled to one another. Although not required, the housing 26 may be configured from at least a first housing component and a second housing component couplable to one another, but this is not required. In some cases, the housing 26 may define and/or facilitate space for one or more inlets leading to the compartment and/or one or more outlets leading from the compartment.

The I/O valves 28 may be any suitable type of valves. In some cases, the I/O valves 28 may be configured to control a passage of fluid through the inlet(s) and/or a passage of fluid through the outlet(s). Further, to facilitate control of the I/O valves 28, the I/O valves 28 may be in electrical communication with a controller (e.g., the controller 36 and/or other suitable controllers).

The rotor 30 may be any suitable type of rotor configured to rotate within the housing 26 (e.g., within the compartment defined by the housing 26) to cause rotation of a fluid mixture received through the inlet(s). In some cases, the rotor 30 may have a disc configuration, a slotted configuration, a cylinder configuration, and/or other suitable configuration for rotating a fluid mixture.

The rotational drive 32 may be any suitable type of drive system configured to cause the rotor 30 to rotate. In one example, the rotational drive 32 may be an electric motor in rotational communication with the rotor 30. In another example, the rotational drive 32 may be an electromagnetic system configured to cause the rotor 30 to rotate when actuated. Other suitable rotational drive configurations are contemplated.

The concentrator 14 may include and/or be in communication with one or more pumps 34. When included, the pump(s) 34 may be any suitable type of pump configured to facilitate moving fluid to and/or from the compartment in which the rotor 30 may be located. The pump 34 may be an optional component (e.g., as represented by the broken rectangle) and when omitted, the rotation of the rotor 30 and/or locations of the inlet(s) and/or outlet(s) may facilitate drawing fluid into the compartment and pushing separated fluid out of the compartment. Although the pump 34 is depicted as being part of the concentrator 14, the pump 34 may be a component that is separate from the concentrator 14 and in fluid communication with the concentrator 14.

The pump 34 may include and/or be in communication with a controller (e.g., the controller 36 and/or other suitable controller). In some cases, the pump 34 may be controlled in coordination with the one or more I/O valves 28 to facilitate providing a fluid to the compartment in which the rotor 30 is located.

The controller 36 may be any suitable controller configured to control or otherwise facilitate control of the concentrator 14, the collector 16, the detector 18, and/or other suitable components of concentration system 10. Further, in some cases, the controller 36 may be configured to process data of or from electrical components of the concentration system 10. The controller 36 may be a component that is separate from the concentration system 10, a component that is separate from other components of the concentration system 10, as depicted in FIG. 2, or a portion or an entirety of the controller 36 may be a component of, or otherwise included in one or more other components of, the concentration system 10.

The illustrative controller 36 may include, among other suitable components, one or more processors 38, memory 40, and/or one or more I/O components 42. Example other suitable components of the controller 36 that are not expressly depicted in FIG. 2 as being part of the controller 36 may include, but are not limited to, communication components, a user interface, a touch screen, a display screen, selectable buttons, a housing, a device or instrument controller, or other suitable components of a controller. As discussed above, one or more components of the controller 36 may be separate from the concentration system 10, separate from other components of the concentration system 10, as depicted in FIG. 2, or may be incorporated into one or more components of the concentration system 10.

The processor 38 of the controller 36 may include a single processor or more than one processor working individually or with one another. The processor 38 may be configured to execute instructions, including instructions that may be loaded into the memory 40 and/or other suitable memory. Example components of the processor 38 may include, but are not limited to, central processing units, microprocessors, microcontrollers, multi-core processors, graphical processing units, digital signal processors, application specific integrated circuits (ASICs), artificial intelligence accelerators, field programmable gate arrays (FPGAs), discrete circuitry, and/or other suitable types of data processing devices.

The memory 40 of the controller 36 may include a single memory component or more than one memory component each working individually or with one another. Example types of memory 40 may include random access memory (RAM), EEPROM, FLASH, suitable volatile storage devices, suitable non-volatile storage devices, persistent memory (e.g., read only memory (ROM), hard drive, flash memory, optical disc memory, and/or other suitable persistent memory) and/or other suitable types of memory. The memory 40 may be or may include a non-transitory computer readable medium. The memory 40 may include instructions stored in transitory and/or non-transitory state on a computer readable medium that may be executable by the processor 38 to cause the processor to perform one or more of the methods and/or techniques described herein.

The I/O components 42 of the controller 36 may include a single I/O component or more than one input-output component each working individually or with one another to interface with one or more devices or users. Example I/O components 42 may be or may include any suitable types of communication hardware or software including, but not limited to, communication ports configured to communicate with the concentrator 14, the collector 16, the detector 18, and/or other suitable computing devices or systems. Example types of I/O components 42 for communication may include wired communication components (e.g., HDMI components, Ethernet components, VGA components, serial communication components, parallel communication components, component video ports, S-video components, composite audio/video components, DVI components, USB components, optical communication components, and/or other suitable wired communication components), wireless communication components (e.g., radio frequency (RF) components, Low-Energy BLUETOOTH protocol components, BLUETOOH protocol components, Near-Field Communication (NFC) protocol components, WI-FI protocol components, optical communication components, ZIGBEE protocol components, and/or other suitable wireless communication components), and/or other suitable I/O components 42. Further, example input device(s) of the I/O components 42 may include, but are not limited to, touch screens, keypads, mice, touch pads, microphones, selectable buttons, selectable knobs, optical inputs, cameras, gesture sensors, eye trackers, voice recognition controls (e.g., microphones coupled to appropriate natural language processing components) and/or other suitable input devices.

Example output device(s) of the I/O components 42 may include, but are not limited to, displays, speakers, vibration systems, tactile feedback systems, optical outputs, and/or other suitable output devices.

When included with or in communication with the controller 36, a user interface may be a set of one or more physical or virtual components configured to communicate with the controller 36 or the concentration system 10 via one or more wired or wireless connections. The user interface may include one or more display devices, one or more I/O components 42, and/or one or more other suitable features or components.

When included with the user interface, display devices may include any suitable display. Example suitable displays include, but are not limited to, touch screen displays, non-touch screen displays, liquid crystal display (LCD) screens, light emitting diode (LED) displays, head mounted displays, virtual reality displays, augmented reality displays, and/or other suitable display types.

Figure 3:
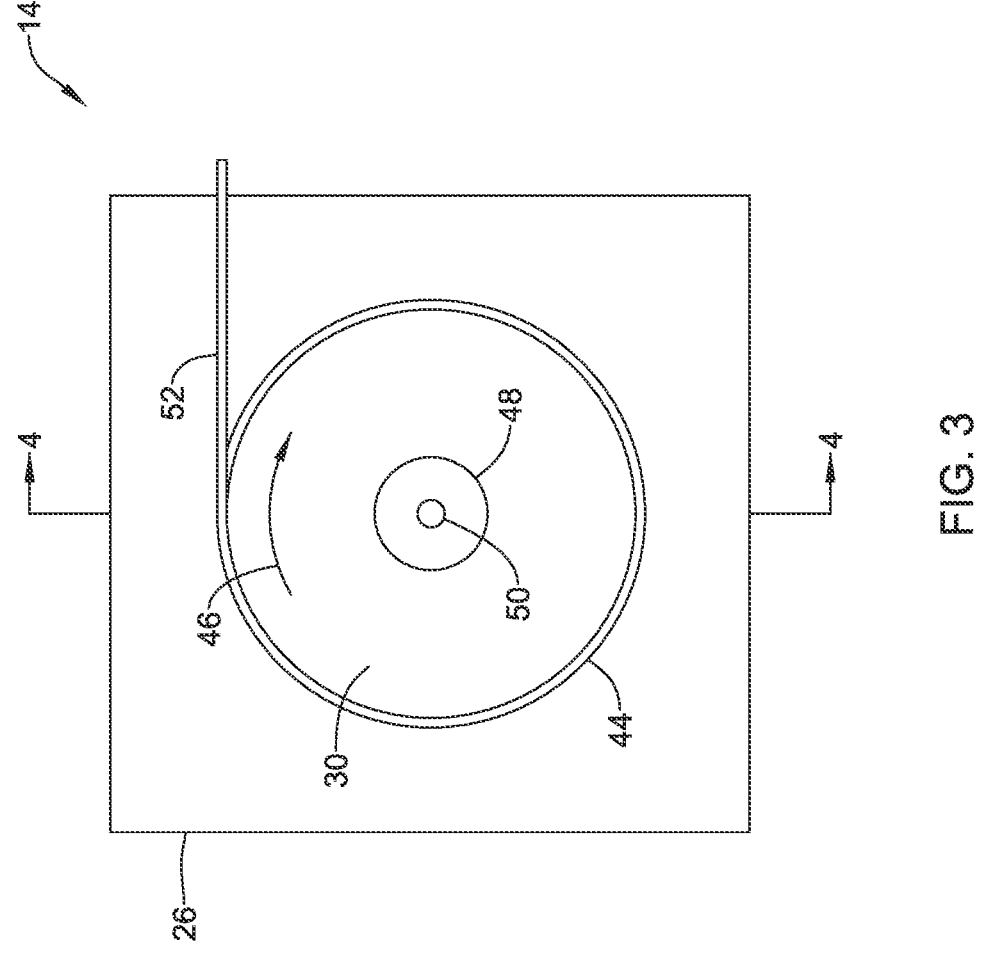
FIG. 3 is a schematic view of an illustrative fluid concentrator, having a portion of a housing removed.

FIG. 3 depicts a schematic view of an illustrative concentrator 14, having a portion of a housing 26 removed such that the rotor 30 in a compartment 44 (e.g., a rotor cavity) may be viewed. In some cases, the concentrator 14 may be a centrifuge machine that rapidly rotates the rotor 30 to apply a centrifugal force to fluid in the compartment 44, which may cause fluids of different mass and/or densities to separate. In one example application, the concentrator 14 may receive a fluid mixture of VOCs and/or other chemical substances from a subject and other fluid in the compartment 44. In the example, rotation of the rotor 30 may cause the fluid mixture to rotate and the resulting centrifugal forces may cause the more dense and/or heavier fluids (e.g., VOCs and/or other chemical substances) in the fluid mixture to separate from less dense and/or lighter fluids (e.g., the other fluid, such as air and/or other suitable gases configured to facilitate movement of the VOCs and/or other chemical substances from the subject to the concentrator 14).

As depicted in FIG. 3, the housing 26 may at least partially define the compartment 44 and the compartment 44 may be configured to allow the rotor 30 to rotate in a direction of arrow 46 and/or other suitable direction and facilitate movement of fluid in the compartment 44 in response to movement of the rotor 30. Alternatively or additionally, the compartment 44 may be entirely or at least partially defined by one or more components other than the housing 26. In some cases, the compartment 44 may take on a shape (e.g., a circular cross-section) similar to the rotor 30 (e.g., a circular cross-section) to facilitate rotation of the fluid in the compartment in response to rotation of the rotor 30.

Although not necessarily required, the housing 26 may be or may at least partially be a rigid housing. Further, at least a portion of the housing 26 may be a stator relative to the rotor 30.

The housing 26 may be formed from any suitable material. Example suitable materials for use in forming the housing 26 include, but are not limited to, metals, polymers, plastics, composite materials, rigid materials, steel, aluminum, brass, polycarbonate, ABS (acrylonitrile butadiene styrene), nylon, and/or other suitable materials or combinations of materials.

The rotor 30 may be formed from any suitable material. Example suitable materials for use in forming the rotor 30 include, but are not limited to, metals, polymers, composite materials, rigid materials, engineered plastics, ceramics, and/or other suitable materials or combinations of materials. In one example configuration, the rotor 30 may be configured to avoid vibration during rotation and/or withstand centripetal forces. Further, the rotor 30 may be configured so as to be balanced about an axis of rotation and avoid wobble as it rotates (e.g., at rotational speeds up to or greater than 100,000 RPM (rotations per minute)).

The rotor 30 may take on any suitable dimensions that facilitate rotation of the rotor 30 in the compartment 44 and movement of fluid in the compartment 44 in response to the rotation of the rotor 30. In some cases, dimensions of the rotor 30 may be selected to impart a desired centrifugal force on a fluid mixture received in the compartment 44, such that heavier and/or denser fluid in the fluid mixture is separated from lighter and/or less dense fluid in the fluid mixture and the heavier and/or denser fluid moves to an outer perimeter of the rotor 30 and/or the compartment 44, while the lighter and/or less dense fluid stays closer to an axis of rotation of the rotor 30. In one example, the rotor 30 may be configured to separate air (e.g., mostly nitrogen and oxygen) or other carrier gas from VOCs and/or other suitable chemical substances from bacteria of a subject that may have a mass and/or density greater than that of the components of air.

The rotor 30 may be coupled to or relative to the housing 26 in any suitable manner that facilitates the rotor 30 rotating relative to the housing 26 and/or the compartment 44. In some cases, the rotor 30 may be rotationally coupled to or relative to the housing 26 with one or more bearings 48.

Any suitable type of bearing 48 may be utilized for coupling the rotor 30 to or relative to the housing 26 and minimizing friction as the rotor 30 spins relative to the compartment 44 and/or the housing 26. Further, utilizing bearings 48 may facilitate eliminating or reducing a need for seals between the rotor 30 and the housing 26. Example suitable types of bearings 48 include, but are not limited to, magnetic bearings, ball bearings, cylinder bearings, oil-filled brass bushings, fluid bearings, Teflon bushings, other suitable mechanisms configured to allow the rotor to spin at a relatively high velocity in a stable fashion (e.g., 10,000 RPMs to 100,000 RPM or greater), and/or combinations of bearing types. In one example, the bearings 48 may be a magnetic bearing type.

Further, the concentrator 14 may include one or more inlets 50 and one or more outlets 52. Although the inlet 50 and/or the outlet 52 may take on other suitable configurations, the inlet 50 may extend axially from exterior the housing 26 into the compartment 44 (e.g., about an axis of rotation of the rotor 30, but this is not required) and through the bearing 48 and the outlet 52 may extend from the compartment 44 to an exterior of the housing 26 in a direction that may be perpendicular to an axis of rotation of the rotor 30. Although not depicted in FIG. 3, the inlet 50 and the outlet 52 may each include one or more valves that facilitate controlling fluid to and/or from the compartment 44.

The inlet 50 and/or the outlet 52 may be defined in any suitable manner. In some cases, the housing 26 may define the inlet 50 and/or the outlet 52. Alternatively or additionally, the inlet 50 and/or outlet 52 may be at least partially defined by a tubular structure having a lumen through which fluid is to pass from an exterior of the concentrator 14 to the compartment 44 and from the compartment 44 to an exterior of the concentrator 14.

Figure 4:
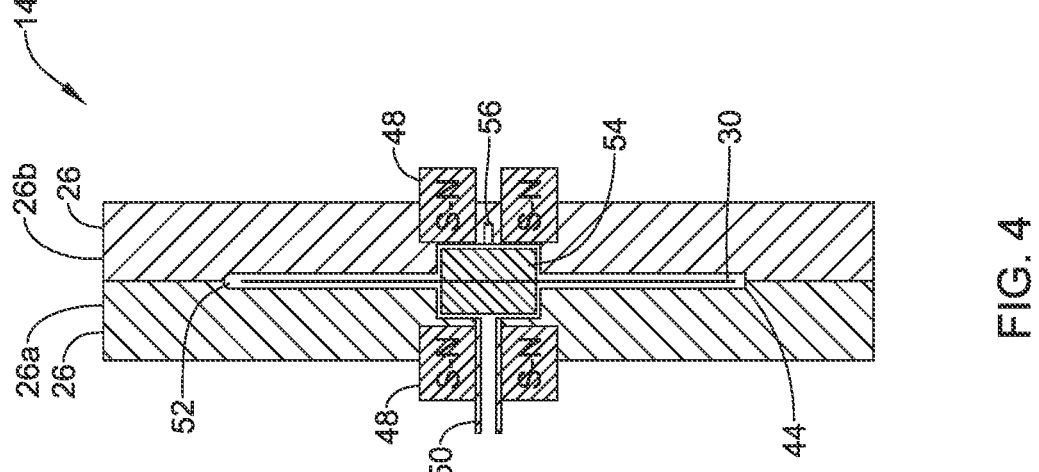
FIG. 4 is a schematic cross-sectional view of the illustrative fluid concentrator depicted in FIG. 3, taken along line 4-4 and with the portion of the housing that is removed in FIG. 3.

FIG. 4 depicts a schematic cross-sectional view of the concentrator 14 depicted in FIG. 3, taken along line 4-4 and with the portion of the housing 26 that was removed in FIG. 3 replaced. As depicted in FIG. 4, the housing 26 may include a first housing portion 26a and a second housing portion 26b, however, other suitable configurations of the housing 26 are contemplated.

When magnetic bearings 48 are utilized and/or in other suitable instances, the rotor 30 may include or may be coupled to one or more magnets 54 and the bearings 48 may be supported by the housing 26 and/or other suitable structure. In some cases, the magnet 54 may be fixed relative to the rotor 30 such that a magnetic field of the magnet 54 may interact with a magnetic field of the bearings 48 (e.g., through the housing 26 or otherwise) to facilitate the rotor 30 rotating in the compartment 44 with minimal friction. In one example, the magnetic forces between the magnet 54 and the bearings 48 may result in the rotor 30 levitating in the compartment 44.

Further, the rotor 30 may include or may be coupled to an axel 56 that, when included, may facilitate maintaining a position of the rotor 30 about an axis of rotation. Although the axel 56 is depicted in FIG. 4 as being positioned within the housing 26, the axel 56 may extend through the housing 26.

The rotor 30 may be caused to rotate in any suitable manner. In some cases, the fields of the magnets 54 and the bearings 48 may interact to cause the rotor 30 to rotate. Alternatively or additionally, an electric motor, field coils, and/or other suitable components may interact with the rotor 30 and/or components coupled to the rotor 30 to cause rotation of the rotor 30. In one example, an electric motor may interact with the axel 56 to cause the axel 56 to rotate and in turn, the rotor 30 to rotate. Other suitable configurations for causing the rotor 30 to rotate are contemplated.

In operation of the concentrator depicted in FIGS. 3 and 4, a fluid mixture (e.g., air or other suitable carrier gas and VOCs and/or other suitable chemicals, and/or other mixture of fluids) may be introduced to the compartment 44 via the inlet 50. As the fluid mixture is introduced to the compartment, valves at the inlet 50 and the outlet 52 may be open. When the inlet and outlet valves are open, an injection of the fluid mixture into the compartment 44 may result in purging the concentrator 14 of other gases. However, the valves at the inlet 50 and the outlet 52 may have other suitable configurations (e.g., open and/or closed) as fluid is introduced to the compartment 44.

A closed valve, as used herein, may mean a valve that is entirely blocking or restricting a flow of fluid at the location of the valve. An opened valve, as used herein, is a valve that is not providing any restriction to or is at least providing less restriction than entirely restricting the flow of fluid at the location of the valve.

The fluid mixture may be injected into the compartment 44 in any suitable manner. Example suitable techniques for introducing fluid into the compartment 44 include, but are not limited to, injecting the fluid mixture with a syringe, a pump (e.g., the pump 32 and/or other suitable pumps), and/or other suitable vessels that are configured to inject or otherwise introduce a fluid mixture to the inlet 50 and the compartment 44.

Once the fluid mixture has been provided to the compartment 44 and previous fluid therein has been purged, the inlet and outlet valves may be closed such that the fluid mixture is sealed inside the concentrator 14. The rotor 30 may then be driven to rotate to a predetermined rotational velocity for a predetermined amount of time of rotation. In one example, the rotor 30 may be caused to rotate at or about a predetermined velocity of 20,000 PRMs for a predetermined period of time in a range of one (1) second to two hundred (200) seconds.

In some cases, the predetermined rotational velocity and/or the predetermined amount of time of rotation may be determined based on the mass and/or densities of the fluids of the fluid mixture and which fluids are to be separated for collecting and/or sensing (e.g., fluid to be sensed) from other fluid of the fluid mixture. But this is not required and the predetermined rotational velocity and/or the predetermined amount of time may be based on one or more other suitable factors. Further, in some cases, the rotational velocity and/or the amount of time of rotation may be adjustable.

Such a rotation of the rotor at a desired rotational velocity for a desired period of time may exert a centrifugal force on the fluid mixture and separate a fluid to be sensed (e.g., VOCs and/or other chemical substances form a subject) of the fluid mixture from other fluid (e.g., air, helium, nitrogen, and/or other suitable carrier fluids) of the fluid mixture. Centrifugal force (F) may be defined by the following equations:

$$F=(m)(v^2/r) \tag{1}$$

$$F=(m)(\omega^2 r) \tag{2}$$

where m is the mass of a moving object (e.g., fluid or other suitable object), v is the velocity of the moving object, r is the distance of the moving object from an axis of rotation, and ω is the angular velocity of the moving body. As the fluid to be sensed may be heavier and/or denser than the other fluid of the fluid mixture, the fluid to be sensed may be driven to an outer perimeter of the compartment 44 and the other fluid of the fluid mixture may remain closer to an axis of rotation of the rotor 30.

In one example of a fluid mixture, the fluid to be sensed may be one or more VOCs and/or other chemical substances from a subject and the other fluid of the fluid mixtures may be a carrier gas of air, which is comprised primarily of nitrogen and oxygen. The molecular weight of molecular nitrogen ($N_2$) is 28 AMU (atomic mass units) and the molecular weight of molecular oxygen ($O_2$) is 32 AMU. Example VOCs and/or other chemical substances from the subject that are to be collected and/or sensed include butane, pentane, 2-Methylheptane, and/or other suitable fluids to be sensed, which all have molecular weights greater than nitrogen and oxygen. For example, butane has a molecular weight of 58 AMU, pentane has a molecular weight of 72 AMU, and 2-Methylheptane has a molecular weight of 114 AMU. When one or more of the VOCs and/or other chemical substances in the example are included with nitrogen and/or oxygen as a carrier gas in a fluid mixture provided to the concentrator, the VOCs and/or other chemical substances would tend to move to an outer perimeter of the compartment 44 in the concentrator 14 in response to rotational movement of the rotor 30 relative to the nitrogen and oxygen.

The above example is illustrative only. One having ordinary skill in the art would experimentally consider a mass/weight, density, and/or other properties of fluids of a fluid mixture to determine how the fluids of the fluid mixture may respond to rotational movement and associated centrifugal acceleration in the concentrator 14. In some cases, relative fluids and/or relative fluid types (e.g., gas, liquid, and/or other suitable fluids) of a fluid mixture may contribute to how the individual fluids in the fluid mixture respond, relative to one another, to rotational movement and associated centrifugal acceleration in the concentrator 14.

Figure 5:
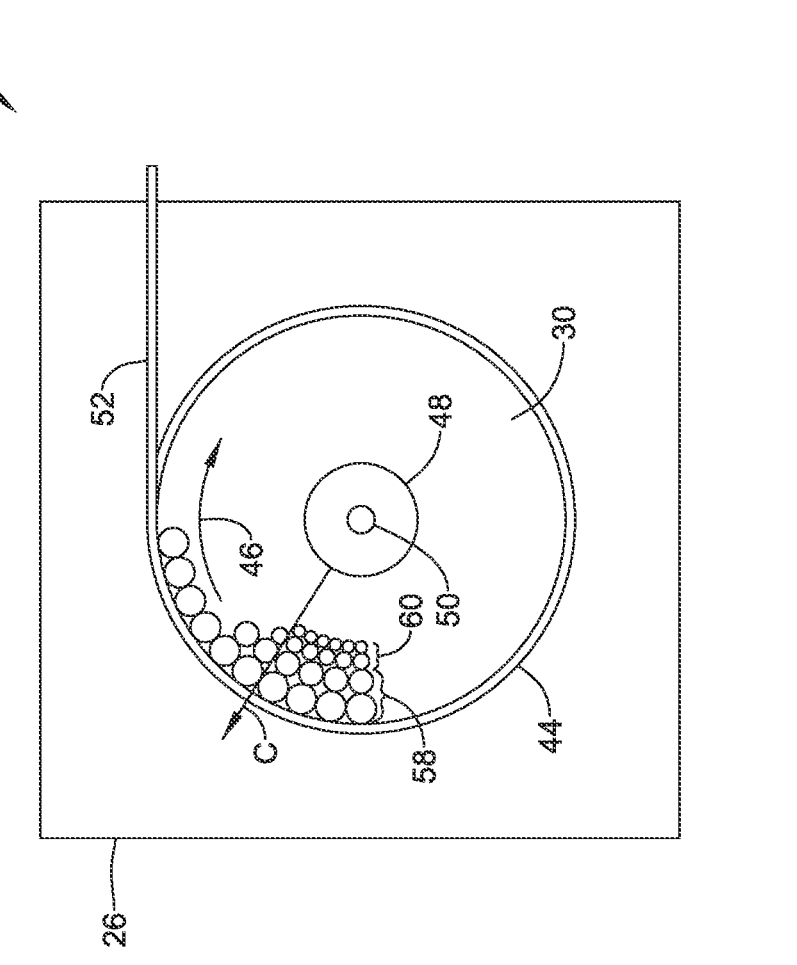
FIG. 5 is a schematic view of an illustrative fluid concentrator in use.

FIG. 5 schematically depicts the concentrator 14 depicted in FIG. 3 with a fluid mixture that has been inserted into the compartment 44 and separated. As the fluid to be sensed 58 is heavier and/or denser than the other fluid 60 (e.g., where the size of the circles may be proportional to the mass and/or density of the fluid, with larger circles representing the denser and/or heavier fluids than the smaller circles), centrifugal forces (e.g., as represented by arrow C) causes the heavier and/or denser fluid to be sensed 58 to separate from the other fluid 60 and move to the outer perimeter of the compartment 44 in response to rotation of the rotor 30 and resulting rotation of the fluid mixture.

Once the fluid to be sensed of the fluid mixture has separated from the other fluid of the fluid mixture, the inlet valve and/or the outlet valve may be opened to cause the fluid to be sensed to exit the compartment 44 through the outlet 52. In some cases, the fluid to be sensed may be driven to the outlet 52 due to rotation of the rotor 30, forces acting on the fluid to be sensed, and a position of the outlet 52. Additionally or alternatively, the fluid to be sensed may be forced to and out of the outlet 52 using an injection technique (e.g., a syringe, a pump, etc.) connected to the inlet that injects a fluid into the compartment under pressure or positive displacement sufficient to drive the fluid to be sensed from the perimeter of the compartment 44 and through the outlet 52. Alternatively, an extraction technique (e.g., a syringe, a pump, etc.) may be utilized at the outlet to withdraw fluid to be sensed from the compartment 44. Further, the other fluid from the fluid mixture may be expelled from the compartment 44 when a next fluid mixture is inserted into the compartment 44 and/or at one or more other suitable times.

In some cases, prior to opening of the inlet valve and/or the outlet valve for extraction of the fluid to be sensed from the compartment 44, the injection technique and/or the extraction technique may be attached to the inlet 50 and/or the outlet 52. Further, a collector configured to collect fluid to be sensed may be in fluid communication with the outlet 52 and/or a detector configured to detect fluid to be sensed may be in fluid communication with the outlet 52, where the collector and/or the detector may be configured to receive the fluid to be sensed from the concentrator 14. As such, through the use of the concentrator 14, fluid to be sensed may include a denser population of VOCs and/or other chemical substances from the subject than may be possible to obtain from the subject without the use of the concentrator 14 due to concentrating the VOCs and/or other chemical substances together.

As an alternative to or in addition to fluidly coupling a collector and/or a detector to the outlet 52 of the concentrator, a collector and/or detector may be positioned entirely around or at one or more locations around a circumference of the compartment 44 in the concentrator 14. In such a configuration, the collector and/or the detector may be directly exposed to concentrated fluid to be sensed that is separated from other fluid of a fluid mixture received in the compartment 44 as the fluids to be sensed are pushed radially outward by centrifugal forces caused by rotation of the rotor 30 and prior or while fluid exits the outlet. The collector and/or the detector configured to be positioned in the concentrator may be reusable or intended for single use.

When utilized in the concentrator 14, the collector and/or detector may be removed from the concentrator 14 after exposure to the fluid to be sensed and transported to or introduced to an analyzer (e.g., a CSA reader) or further detector for analysis. Alternatively or additionally, when the housing and/or other components of housing 26 are formed from a transparent material, the detector may read or otherwise analyzed through the housing 26. Further, the concentrator 14 may include an analyzer configured to analyze detectors exposed to the separated fluid to be sensed.

Figure 6:
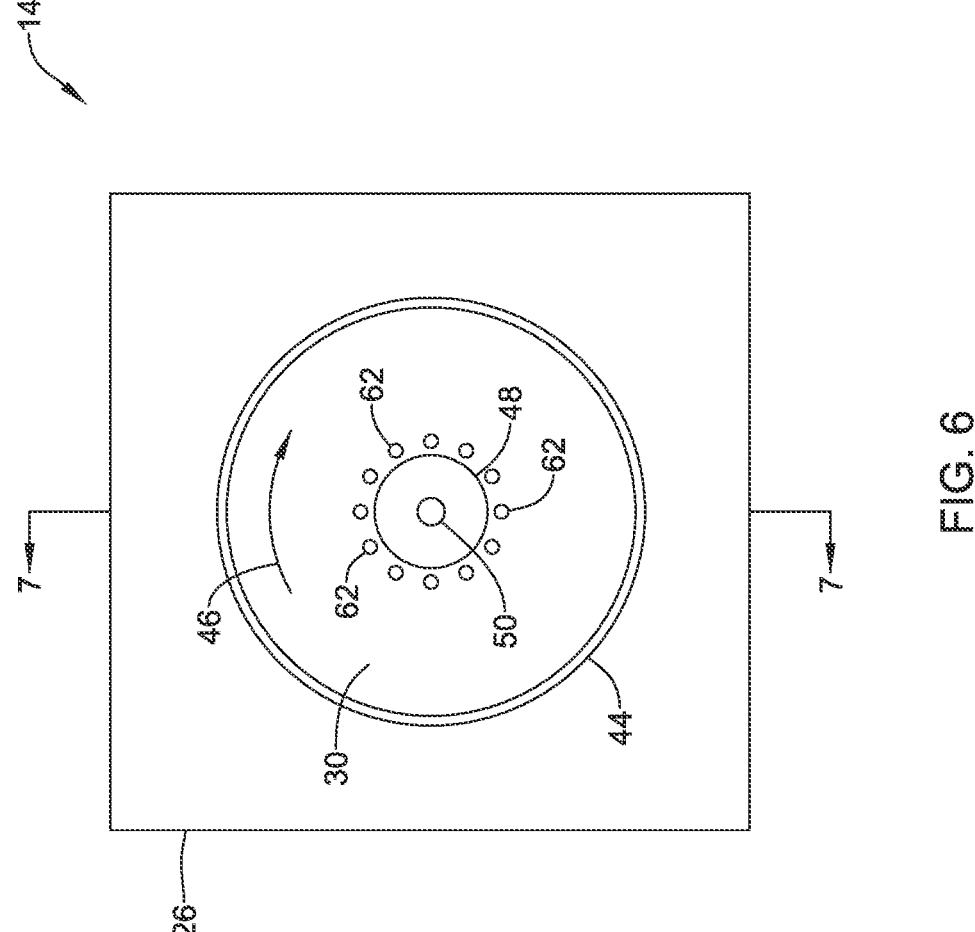
FIG. 6 is a schematic view of an illustrative fluid concentrator, having a portion of a housing removed.
Figure 7:
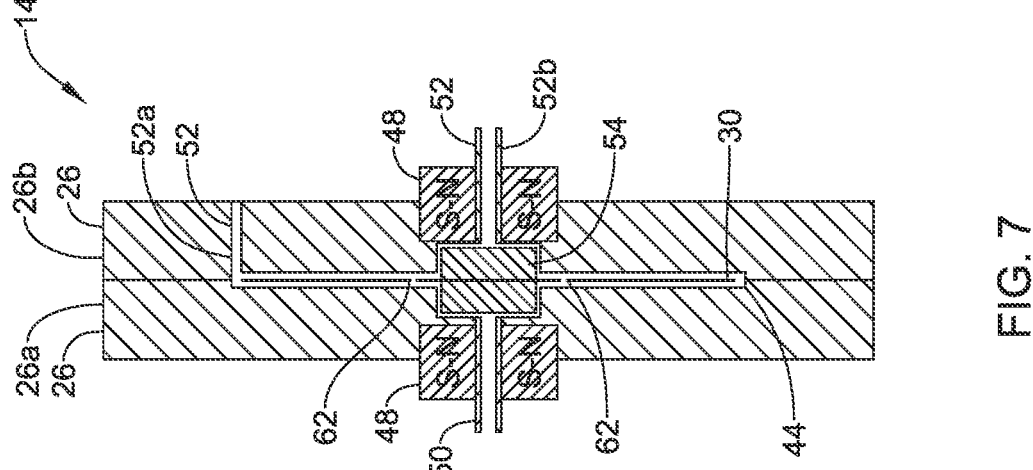
FIG. 7 is a schematic cross-sectional view of the illustrative fluid concentrator depicted in FIG. 6, taken along line 7-7 and with the portion of the housing that is removed in FIG. 6.

FIGS. 6 and 7 depict views of the concentrator 14 similar to as shown in FIGS. 3 and 4, where the rotor 30 includes one or more fluid bypass holes 62 and one or more outlets 52 extend from the compartment 44 to exterior the housing 26 in a direction parallel, substantially parallel, and/or non-perpendicular to an axis of rotation of the rotor 30. FIG. 6 depicts a schematic view of the concentrator 14 with a portion of the housing 26 removed. FIG. 7 depicts a schematic cross-sectional view of the concentrator 14 of FIG. 6, taken along line 7-7 and with the portion of the housing removed in FIG. 6 added in.

As depicted in FIG. 6, the rotor 30 may include a plurality of fluid bypass holes 62 configured to facilitate moving other fluid (e.g., a carrier fluid) of the fluid mixture that is separated from the fluid to be sensed to a carrier fluid outlet (e.g., the output for waste/recirculation put 24 and/or other fluid output). In one example, the rotor 30 may include twelve (12) fluid bypass holes 62, but other suit configurations of the fluid bypass holes 62 through the rotor 30 are contemplated.

As depicted in FIG. 7, the concentrator 14 may have a first outlet 52a and a second outlet 52b. The first outlet 52a may be a fluid to be sensed outlet and may be fluidly coupled to a collector and/or detector. The second outlet 52b may be an outlet for the other fluid (e.g., a carrier gas) of the fluid mixture. The first outlet 52a for the fluid to be sensed may be positioned proximate an outer perimeter of the compartment 44 and the second outlet 52b for the other fluid of the fluid mixture may be located radially proximal relative to the first outlet 52a. Similar to as discussed above with respect to FIGS. 3 and 4 and although not depicted, the inlet 50, the first outlet 52a, and the second outlet 52b may include one or more valves for controlling a flow of fluid through the concentrator 14.

In operation of the concentrator 14 depicted in FIGS. 6 and 7, the fluid inlet 50 may be connected to a flow of fluid mixture from a headspace at or about a target location on a subject, the first fluid outlet 52a may be fluidly coupled to a connector and/or detector and may output fluid to be sensed that is separated from the fluid mixture received in the compartment 44, and the second fluid outlet 52b may allow the carrier fluid or other fluid separated from the fluid mixture to be exhausted from the compartment 44 and/or returned to the headspace at or about a target location of the subject. In some cases, a pump (not shown) may be utilized to pump a fluid mixture from the headspace at or about a target location of the subject to and/or through the compartment 44.

The rotor 30 may be driven, as discussed herein or otherwise, to rotate at a rotational velocity for an amount of time of rotation so as to exert centrifugal force on the fluid mixture and separate fluid to be sensed from other fluid of the fluid mixture. In one example, the rotor 30 may be caused to rotate at or about a velocity of 20,000 RPMs for a period of time in a range of one (1) second to two hundred (200) seconds. The separated fluid to be sensed from the fluid mixture may exit the compartment 44 through the first outlet 52a to a collector and/or a detector. The separated other fluid of the fluid mixture may exit the compartment 44 through the second outlet 52b.

The valves at the inlet 50 and the outlets 52 (e.g., the first outlet 52a and the second outlet 52b) may have any suitable configuration (e.g., open/closed configuration) as the rotor 30 rotates or is otherwise driven. For example, all of the valves situated at the inlet 50, the first outlet 52a, and the second outlet 52b may be open while the rotor 30 rotates, may be closed as the rotor 30 rotates, and/or one or more valves maybe open and one or more valves may be closed as the rotor 30 rotates.

In some cases, the valves may have a desired open or closed position when the rotor 30 initiates rotation and/or during rotation, and then, after a period of time, one or more of the valves may be adjusted to the other of the open or closed position. In one example, the valves at the first outlet 52a and the second outlet 52b may be initially closed as the rotor 30 rotates and after a first period of time, the second outlet 52b may be opened to the allow the separated other fluid to flow out of the concentrator 30 and allow further fluid mixture to be provided to the compartment 44 via the inlet 50 for separation. In such a configuration, the separated fluid to be sensed may accumulate while the separated other fluid may be exhausted from the concentrator 14 and after a second period of time, the first outlet 52a may be opened to exhaust the fluid to be sensed from the concentrator.

A closed valve, as used herein, may mean a valve that is entirely blocking or restricting a flow of fluid at the location of the valve. An opened valve, as used herein, is a valve that is not providing any restriction to or is at least providing less restriction than entirely restricting the flow of fluid at the location of the valve.

Figure 8:
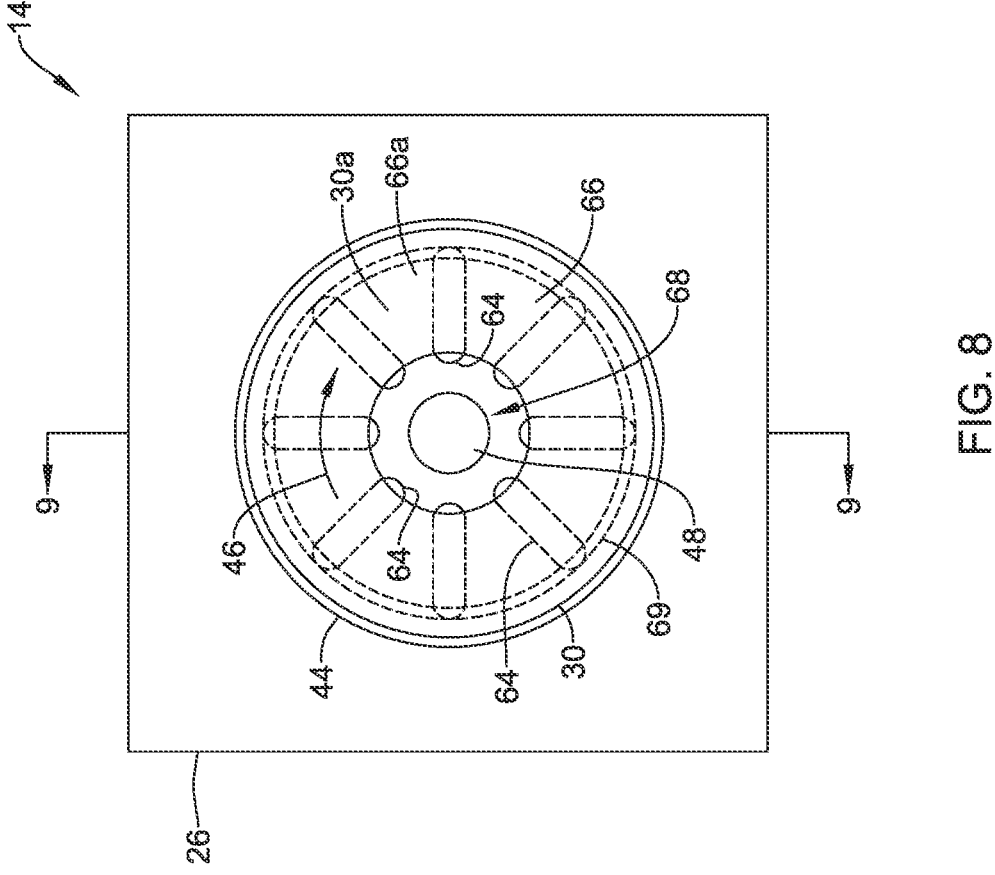
FIG. 8 is a schematic view of an illustrative fluid concentrator, having a portion of a housing removed.
Figure 9:
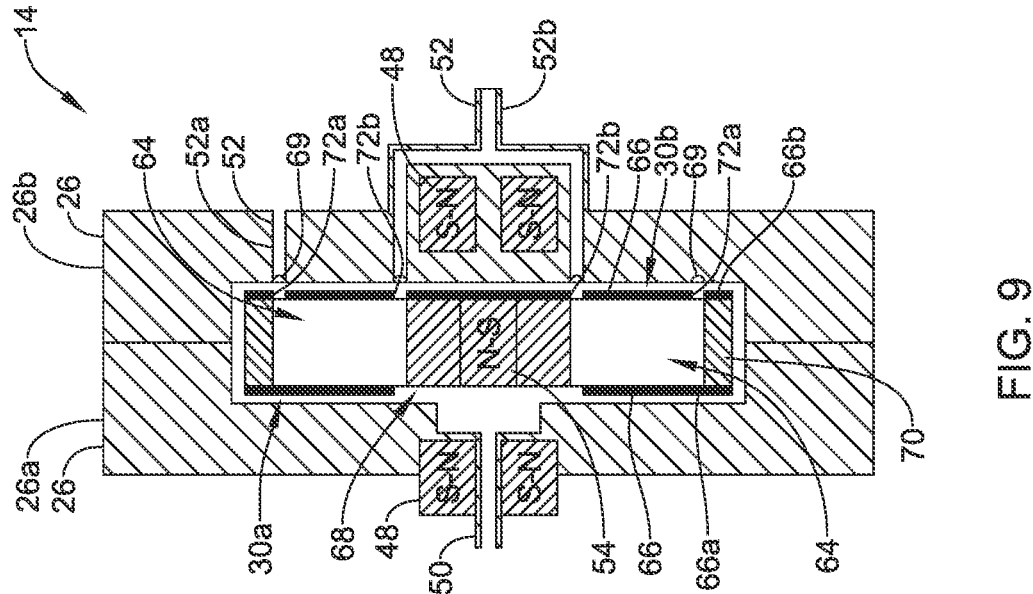
FIG. 9 is a schematic cross-sectional view of the illustrative fluid concentrator depicted in FIG. 8, taken along line 9-9 and with the portion of the housing that is removed in FIG. 8.

FIGS. 8 and 9 depict an illustrative concentrator 14 having a rotor 30 with a thickness that is greater than a thickness of the rotor 30 depicted in FIGS. 3-7 and one or more radial slots or other opening extending through the height of the rotor 30 from a first side 30a to an opposing second side 30b. Unless indicated otherwise, the concentrator 14 may be similarly configured to the other concentrators 14 discussed herein.

FIG. 8 depicts the schematic view of the concentrator 14 with a portion of the housing 26 removed, where the rotor 30 may include eight (8) slots 64, but other suitable quantities of slots 64 are contemplated. Although the rotor 30 may take on other suitable configurations, the rotor 30 may include one or more covers 66 at least partially covering the slots 64 defined by a base structure. In one example, the rotor 30 may a include first cover 66a extending over at least a portion of the slots 64 and defining an opening 68 through which a fluid mixture from inlet 50 may flow into the slots 64.

Further, the housing 26 and/or other suitable component of the concentrator 14 may define a channel 69. The channel 69 may be in communication with the slots 64 and may be configured to receive fluid to be sensed that is separated from the other fluid of the fluid mixture received in the slots 64.

FIG. 9 depicts a schematic cross-sectional view of the concentrator 14 of FIG. 8, taken along line 9-9 and with the portion of the housing 26 removed in FIG. 6 added in. As depicted in FIG. 9, the housing 26 may define the inlet 50, the first outlet 52a, and the second outlet 52b, but this is not required and additional or alternative components may define the inlet 50, the first outlet 52a, the second outlet 52b, and/or one or more other suitable inlets and/or outlets.

The rotor 30 depicted in FIG. 9 may include a structure 70 in which the slots 64 may be defined, the first cover 66a at a first side of the structure 70, and a second cover 66b at a second side of the structure 70 opposite the first side of the structure 70. A thickness of the first cover 66a, a thickness of the second cover 66b, and a thickness of the structure 70 may be summed to arrive at the thickness of the rotor in FIGS. 8 and 9. The first cover 66a, the second cover 66b, and the structure 70 may be formed from the materials discussed herein for forming the rotor 30 and/or other suitable materials.

The covers 66 may be coupled to the structure 70 by any suitable connection technique including, but not limited to, an adhesive connection, a welding connection, and/or other suitable connection technique. Further, in some cases, the covers 66 may be monolithically or unitarily formed with the structure 70.

As discussed with respect to FIG. 8, the first cover 66a may define the opening 68 for receiving a fluid mixture from the inlet 50 and into the slots 64. The second cover 66b may overlap the slots 64 and define exit or outlet ports 72a, 72b configured to allow separated fluids to exit the slots 64. In some cases, the exit ports 72a, 72b may align with outlets 52. In one example, the one or more first exit or outlet ports 72a may be configured to output fluid to be sensed that is separated from a received fluid mixture and may be aligned with the channel 69 and the first outlet 52a located proximate to a radial perimeter of the compartment 44. In another example, one or more second exit or outlet ports 72b may be located radially inward from the first exit or outlet ports 72a and may be configured to output other fluid (e.g., a carrier fluid) that is separated from a received fluid mixture and may be aligned with the second outlet(s) 52b positioned nearer an axis of rotation of the rotor than the first outlet 52a.

The configuration of the concentrator 14 depicted in FIGS. 8 and 9 may be configured to increase a volume of fluid mixture from a subject that may be accelerated and separated at a time due to the slot configuration and the positioning of the outlets 52. Further, utilizing the covers 66 may reduce rotational loss by shielding the fluid mixture received in the fluid compartment 44 (and the slots 64) from stationary walls of the housing 26 that may resist rotation and encourage remixing of the gases and VOCs. The configuration of the rotor 30 in FIGS. 8 and 9 may be utilized with other concentrator configurations discussed herein and/ or other suitable concentrators.

Figure 10:
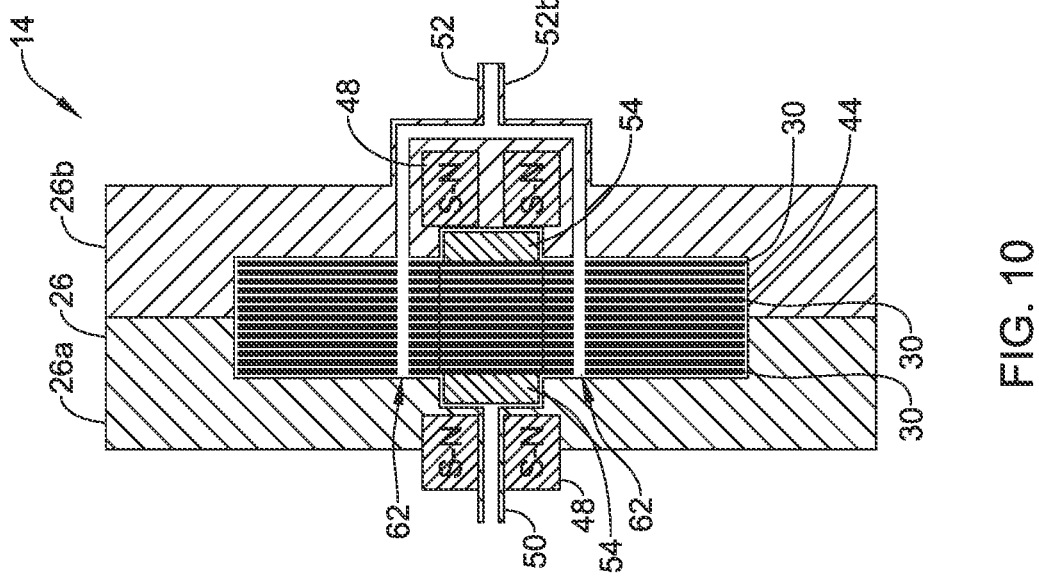
FIG. 10 is a schematic cross-sectional view of an illustrative fluid concentrator system.

FIG. 10 depicts a cross-sectional view of an illustrative concentrator 14 having a plurality of rotors 30 in the compartment 44 defined by the housing 26. Although the concentrator 14 depicted in FIG. 10 includes thirteen (13) rotors 30, it is contemplated that two or more rotors may be utilized.

Each of the rotors 30 utilized in the concentrator 14 having a plurality of rotors 30 may have any suitable configuration or combinations of configurations discussed herein or otherwise. As depicted in FIG. 10, the rotors 30 may have fluid bypass holes 62 in a configuration similar to the rotors 30 discussed above with respect to FIG. 7, but this is not required.

The housing 26 of the concentrator 14 comprising a plurality of rotors 30 in the compartment 44 may have any suitable number of outlets 52. In the configuration of housing 26 depicted in FIG. 10, the housing 26 may define a first outlet (not shown in FIG. 10) that extends from the compartment 44 to an exterior of the housing 26. This first outlet may be similarly configured to the outlet 52 depicted in FIG. 3 or otherwise configured. The first outlet may be configured in the housing 26 to output fluid to be sensed that is separated from a received fluid mixture. Additionally, the housing 26 may define a second outlet 52b configured to exhaust other fluid (e.g., carrier gas) separated from the fluid mixture received in the compartment 44, which may be directed toward the second outlet 52 by the fluid bypass holes 62 in the rotors 30.

In operation of the concentrator 14 comprising a plurality of rotors 30 in the compartment 44, the concentrator 14 may receive a fluid mixture in the compartment 44 from a target location at or about a subject and the valves at the inlet and the outlet may be opened, as discussed herein, or in one or more other suitable configurations. The rotors 30 may be rotated, as discussed herein, and fluid to be sensed may be separated from other fluid of the fluid mixture and pushed by centrifugal forces toward the outer perimeter of the compartment 44 and to the first outlet (not shown) for collection in a collector, detection in a detector, further processing, etc. In some cases, a detector and/or analyzer may be included in the concentrator 14, as discussed herein, and the fluid to be sensed may be detected and/or analyzed while in the concentrator 14.

The other fluid (e.g., the carrier gas) of the fluid mixture may be passed to a next rotor 30 of the plurality of the rotors 30 in the compartment 44 where additional fluid to be sensed may be separated from the other fluid. This process may continue until the fluid has passed through all of the rotors 30 in the compartment 44 and any remaining other fluid of the fluid mixture may be outputted from the concentrator 14 through the second outlet 52b.

Figure 11:
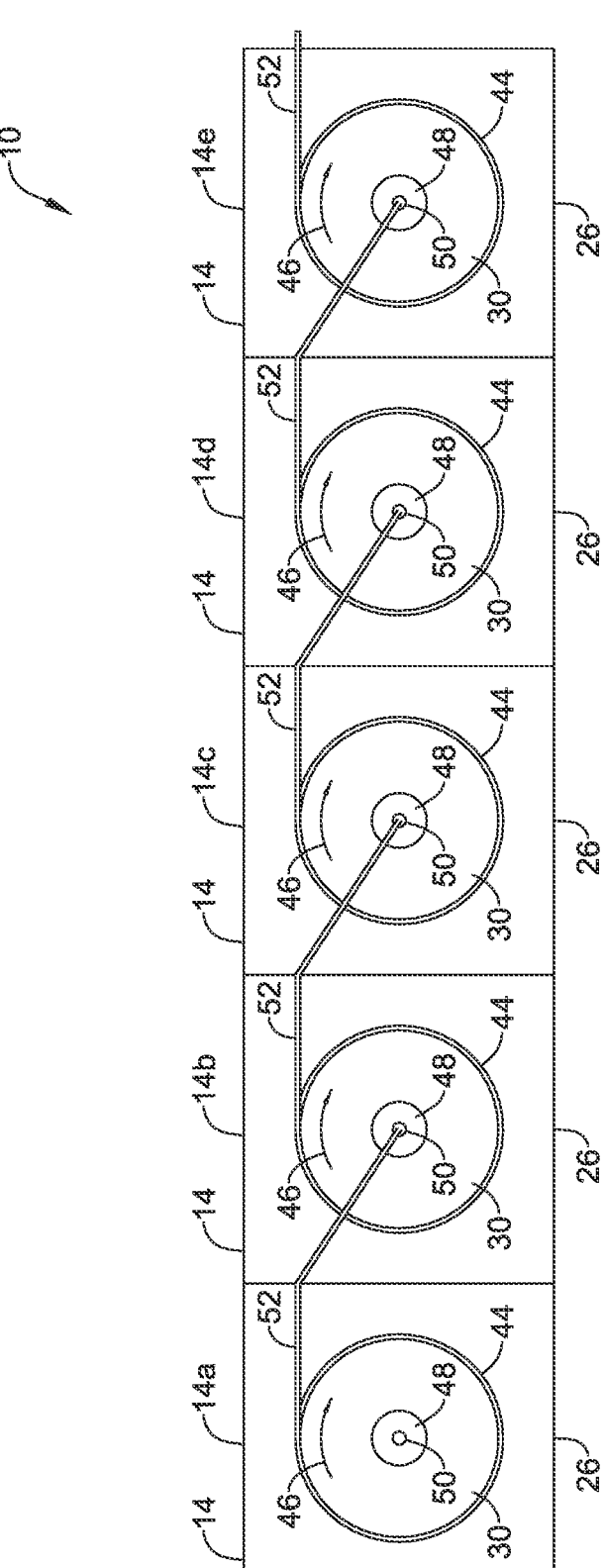
FIG. 11 is a schematic view of an illustrative fluid concentrator system.

FIG. 11 depicts a schematic diagram of a concentration system 10 having a plurality of concentrators 14 fluidly coupled in a linear array series, where each of the concentrators 14 have a portion the housing 26 removed. The concentrators 14 depicted in FIG. 11 may be similarly configured to one or more of the other concentrators 14 discussed herein or otherwise configured.

The concentration system 10 having a plurality of concentrators 14 arranged in a linear series may include two or more concentrators 14. As depicted in FIG. 11, the concentration system 10 may include five concentrators 14a, 14b, 14c, 14d, 14e arranged in series, wherein a first concentrator 14a may be configured to receive a fluid mixture including VOCs and/or other chemical substances from a target location at or about a subject and a fifth concentrator 14e (or a last concentrator 14 of a concentrator system having N concentrators) may be configured to output a concentrated fluid to be sensed.

Although not depicted in FIG. 11, the concentrators 14 of the concentration system 10 depicted in FIG. 11 may include one or more outlets for outputting other fluid (e.g., carrier gas, etc.) separated from the fluid received in each of the concentrators 14. Similar to as discussed herein, the output of the other fluid may be exhausted to atmosphere, stored, provided back to the target location at or about the subject, further processed with one or more concentrators 14, and/or processed in one or more other suitable manners.

In operation, a fluid mixture from a target location at or about a subject may be introduced to the inlet 50 of the first concentrator 14a. Similar to as discussed herein, the fluid mixture may be processed in the first concentrator 14a in response to rotation of the rotor 30 and the heavier and/or denser fluids to be sensed may be driven by centrifugal forces to an outer perimeter of the rotor 30 and/or the compartment 44. As the rotor rotates and/or in response to one or more other positive or negative pressures, the fluids to be sensed may exit the first fluid concentrator 14a through the outlet 52 and follow a fluid path to the inlet 50 of the next concentrator 14 in the series (e.g., the second fluid concentrator 14b, in the example of FIG. 11).

Although the fluid to be sensed that exits the outlet 52 may include a concentrated concentration of analyte (e.g., VOC and/or other suitable chemical substances from the subject), there may be some other fluid from the fluid mixture provided to the first concentrator 14*a* remaining in the fluid to be sensed because the concentrators 14 may not be 100% efficient. As such, to further concentrate fluid to be sensed, the fluid to be sensed that is output from the first concentrator 14*a* may be further concentrated by the second concentrator 14*a* in the manner described herein. Such successive concentration may continue as the fluid output from one concentrator 14 is processed by a next concentrator 14 in the series of the system 10 until a last concentrator 14 (e.g., the fifth concentrator 14*e*, as depicted in FIG. 11) is reached and/or a desired purity of analyte is reached in the fluid to be sensed. The fluid output by the last concentrator 14 or the concentrator 14 at which a desired purity in the fluid to be sensed is reached may be provided to a collector and/or a detector for analysis, as discussed herein.

Figure 12:
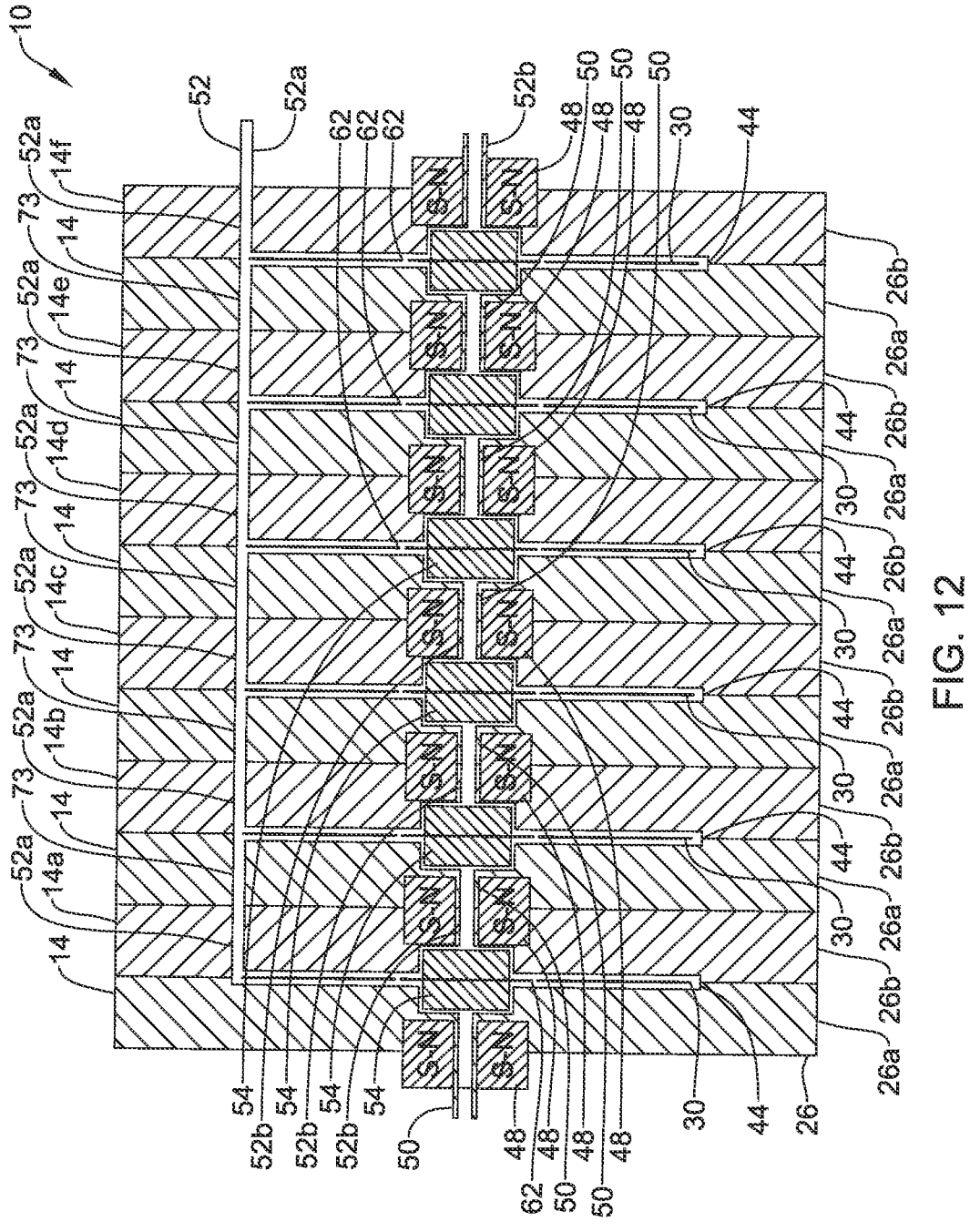
FIG. 12 is a schematic cross-sectional view of an illustrative fluid concentrator system.

FIG. 12 depicts a schematic diagram of a concentration system 10 having a plurality of concentrators 14 fluidly coupled in a coaxial, stacked series. The concentrators 14 depicted in FIG. 12 may be similarly configured to one or more of the other concentrators 14 discussed herein or otherwise configured.

The concentration system 10 having a plurality of concentrators 14 arranged in a stacked series may include two or more concentrators 14. As depicted in FIG. 12, the concentration system 10 may include six concentrators 14*a*, 14*b*, 14*c*, 14*d*, 14*e*, 14*f* arranged in coaxial, stacked series, wherein a first concentrator 14*a* may be configured to receive a fluid mixture including VOCs and/or other chemical substances from a target location at or about a subject and a sixth concentrator 14*f* (or a last concentrator 14 of a concentrator system having N concentrators) may be configured to output a concentrated fluid to be sensed through a first outlet 52*a* and other fluid (e.g., a carrier fluid) from the fluid mixture through a second fluid outlet 52*b*.

The concentrators 14 of the concentration system 10 depicted in FIG. 12 may include one or more outlets 52 for outputting separated fluid from the fluid mixture, as discussed herein. For example, the housing 26 may define a first outlet 52*a* located adjacent an outer perimeter of the rotor 30 and/or the compartment 44 that is configured to output fluid to be sensed and a second outlet 52*b* at or nearer an axis of rotation of the rotor 30 than the first outlet 52*a*.

The first outlets 52*a* of each concentrator 14 may be in fluid communication with one another. In one example, as depicted in FIG. 12, the first outlets 52 may be in fluid communication with one another via a flow path 73 extending through the first housing portion 26*a* of the housing 26, but other suitable configurations for fluidly coupling the first outlets 52*a* are contemplated. A fluid outlet 52*a* of a last concentrator in the series of concentrators may output fluid to be sensed to a collector, a detector, and/or other suitable component.

The second outlets 52*b* of each concentrator 14 may output other fluid (e.g., carrier fluid, etc.) separated from the fluid received in each of the concentrators 14. The output of the second outlets 52*b* of the concentrators 14 axially stacked in a series may align with an inlet 50 of a next concentrator 14 in the series. As such, an output of the other fluid separated from the fluid mixture may be output from the second fluid outlet 52*b* to a next concentrator 14 for processing through the inlet 50 of the next concentrator 14. Similar to as discussed herein, the output of the other fluid through the last concentrator 14 in the axially stacked series (e.g., the sixth concentrator 14*f*, as depicted in FIG. 12) may exhaust any remaining other fluid from the fluid mixture to atmosphere, to storage, back to the target location at or about the subject, and/or to one or more other locations for processing or storage.

In operation, a fluid mixture from a target location at or about a subject may be introduced to the inlet 50 of the first concentrator 14*a*. Similar to as discussed herein, the fluid mixture may be processed in the first concentrator 14*a* in response to rotation of the rotor 30 and the heavier and/or denser fluids to be sensed may be driven by centrifugal forces to an outer perimeter of the rotor 30 and/or the compartment 44 while the lighter and/or less dense other fluid of the fluid mixture may remain closer to an axis of rotation of the rotor 30. As the rotor rotates and/or in response to one or more other positive or negative pressures, the fluids to be sensed may exit the first fluid concentrator 14*a* through the first outlet 52*a* and follow a flow path 73 to the first outlet 52*a* of a next concentrator 14 in the series until a last concentration 14 is reached and then, to a collector and/or to a detector. Similarly, separated other fluid of the fluid mixture may exit the first fluid concentrator 14*a* through the second outlet 52*b* to a fluid inlet 50 of the next concentrator 14 in the series (e.g., the second fluid concentrator 14*b*, in the example of FIG. 12), to atmosphere, back to the target location at or about the subject, and/or to one or more other locations.

Although the fluid to be sensed has been separated from the other fluid of the fluid mixture, the other fluid separated from the fluid mixture using the first concentrator 14*a* may continue to contain fluid to be sensed (e.g., analyte) because the concentrators 14 may not be 100% efficient. As such, to further concentrate fluid to be sensed, the other fluid of the fluid mixture that is output from the first concentrator 14*a* may be further processed by the second concentrator 14*b* in the manner described to separate out additional fluid to be sensed. Such successive concentration may continue as the fluid output from one concentrator 14 is processed by a next concentrator 14 in the axially stacked series of concentrators 14 of the system 10 until a last concentrator 14 (e.g., the sixth concentrator 14*f*, as depicted in FIG. 12) is reached and/or a desired purity of analyte is reached in the fluid to be sensed. The fluid to be sensed that is output from the concentrators 14 axially stacked in series may be combined through the flow paths 73 and the first outlets 52*a*, output form the first outlet 52*a* of the last concentrator 14 or a concentrator 14 at which a desired purity in the fluid to be sensed is reached, and then may be provided to a collector and/or a detector for analysis, as discussed herein.

Further, although not necessarily depicted in FIG. 12, fluid mixture from a subject that is in fluid communication with the inlet 50 of the first concentrator 14 (e.g., the contractor 14*a* in FIG. 12) in the axially aligned series of concentrators 14 may also be provided to the inlets 50 of all of or at least one or more of the other concentrators 14 of the axially aligned series of concentrators 14. Though not required, providing the fluid mixture to the inlets 50 of each or at least two or more concentrators 14 in the series of concentrators 14 may facilitate separating fluid to be sensed from the fluid mixture and from the other fluid passed between adjacent concentrators 14 by ensuring the other fluid that is processed in the concentrators 14 remains near an axis of rotation of the rotor (e.g., near the bypass holes 62) for outputting through the second outlet 52*b* due to the heavier fluids (e.g., from the other fluid transferred between the concentrators 14 and the additional fluid mixture) moving toward an outer perimeter of the rotors 30 and the compartment 44 during rotation of the rotors 30 and crowding out or blocking the other fluid being processed.

In some cases, the rotors 30 of one or more concentrator 14 of the concentrators 14 axially arranged in series or otherwise arranged may be individually controlled to rotate at different or similar speeds, different or similar times, and/or for different or similar periods of time. In one example, the rotor 30 of a second concentrator 14 in an axially arranged series of rotors 30 as depicted in FIG. 12 may be controlled to rotate at a rate and for a period of time such that only fluids to be sensed that remain in the other fluid outputted from a previous concentrator 14 are pushed to an outer perimeter of the rotor 30 and/or the compartment 44 in which the rotor is located and to the first outlet 52*a*. When the speed and duration of rotation of the rotor 30 is controlled in such a manner, the chances of the other fluid (e.g., the carrier fluid, etc.) of the fluid mixture moving to the outer perimeter of the rotor 30 and the compartment 44 to the first outlet 52*a* may be mitigated. Other suitable configurations of speed, timing, and duration may be utilized to facilitate concentrating and outputting fluid to be sensed from concentrators 14 arranged in series or otherwise arranged.

In some cases, control valves associated with the inlet 50 and/or the outlets 52 of the one or more concentrators 14 arranged axially in series or otherwise arranged may be individually controlled to facilitate passing fluid through the inlets 50 and/or outlets 52 of the concentrators 14. In one example, the valves associated with the first outlet 52*a* and the second outlet 52*b* may be closed as a fluid is inserted into the inlet of the concentrators 14 axially arranged in series. Then, as the rotor 30 is rotated, the valve associated with the second outlet 52*b* may be opened to output the other fluid of the fluid mixture from the concentrator 14. Once the other fluid has been outputted, the valve associated with the second outlet 52*b* may be closed and the valve associated with the first outlet 52*a* may be opened to output any separated fluid to be sensed. The valve at the fluid inlet 50 may be opened or closed while fluid is output through the outlets 52, as desired. When valves associated with the inlet 50 and/or the outlet 52 are controlled in such a manner, the chances of the other fluid (e.g., the carrier fluid, etc.) of the fluid mixture moving to the outer perimeter of the rotor 30 and the compartment 44 to the first outlet 52*a* may be mitigated. Other suitable valve configurations may be utilized to facilitate concentrating and outputting fluid to be sensed from concentrators 14 arranged in series.

Through the repeated processing of the other fluid of fluid received at a concentrator 14, the amount of fluid to be sensed that is separated from the fluid mixture received may be increased relative to processing the fluid a single time. In some cases, the systems 10 of the example configurations in FIGS. 11 and 12 may be used in combination with one another to further maximize separating fluid to be sensed of a received fluid mixture from other fluid of the fluid mixture.

The configurations of the concentration systems 10 and the concentrators 14 discussed herein may be used with the following general method, among other methods: 1) connecting an outlet (e.g., a first outlet 52*a*, as discussed herein, and/or other suitable outlet) for a fluid to be sensed to a VOC detection device, 2) initiating rotation of a rotor (e.g., the rotor 30 and/or other suitable rotor) of a concentrator (e.g., the concentrator 14 and/or other suitable concentrator), 3) introducing a fluid mixture, as discussed herein, from a headspace of a collection device at a target location of a subject or storage vessel to an inlet (e.g., the inlet 50 and/or other suitable inlet) of the concentrator, 4) opening a valve at the fluid to be sensed outlet to allow fluid to be sensed (e.g., a fluid with concentrated VOCs) to flow into the VOC detection device or adsorbent material. In some configurations, an additional or alternative step may include returning the fluid to be sensed (e.g., a fluid with concentrated VOCs) to the headspace after processing in the VOC detection device. Once detection is complete, a valve for the outlet can be shut again. In another additional or alternative configuration, the method may include connecting a pump to drive a fluid mixture from a headspace at a target location of or about skin of a subject into the inlet of the concentrator to provide a continuous flow of headspace fluid mixture to the concentrator, and a continuous flow of concentrated fluid to be sensed to the concentrator outlet for some period of time sufficient to accurately analyze the VOCs.

In some configurations of the concentration systems 10 discussed herein, readings of the analyte concentration of the fluid to be sensed may be made while a collector or other suitable device remains sealed or proximate to the subject's target location (e.g., skin, wound, and/or other anatomy) and the analytes are concentrated in the concentrator. This method can minimize cross-contamination or dilution which may be caused by the surrounding environment or handling. In this configuration, the concentration of analyte can be a continuous process during the reading of the analytes, providing a temporal parameter that can be additionally useful for assessment of bacteria type and quantity.

At faster rotational speeds, the separation between fluid to be sensed from a fluid mixture of various fluids with various mass and/or densities may be increased. At slower speeds, there may be less separation and more mixing of the VOCs inside the concentrator chamber. Thus, by sampling a fluid at the periphery of the rotor at various speeds, an assessment can be made as to the relative concentrations of different fluid to be sensed contained within a concentrator. Further, in some cases, selection of rotational speeds of the rotor may facilitate stratifying fluids from lightest and/or least dense to heaviest and/or densest as the fluids radially align outward from a rotational axis of the rotor. Using different rotational speeds to configure the separated fluid may be useful for identification of bacterial strains, especially those strains that produce the same or similar VOCs but at slightly different concentrations. The measurement of the ratio of different VOCs can also help to identify the stage of the bacterial colony in its lifecycle. Similarly, in multistage concentrators, such as those depicted in FIGS. 11 and 12 and/or other suitable configurations, the relative concentrations of different VOCs detected near the periphery of the rotor chamber in each concentrator unit can provide valuable information about the relative concentration of different VOCs in the original sample from the wound or skin.

Data collected about the rotational speed of the rotor or rotors, VOCs collected at each rotational speed, or at each stage of a multistage concentrator can all be analyzed using a computer system (e.g., a controller). Machine learning algorithms can be derived and trained using known VOCs or known bacterial strains or combinations of bacterial strains in order to generate an intelligent software system for analysis of bacterial strain, quantity, lifecycle stage, and for detecting and analyzing combinations of bacteria that may be present in a single wound. Such a computer system may include a microprocessor for processing the data and running the software and algorithms, a computer hard drive or electronic memory for storing the data, and a user interface.

It will be understood that in any of the embodiments described above, the separation of fluids and analysis of detected analytes can be used to identify bacteria in a wound, on skin, and/or to identify illnesses that alter the patient's metabolism in a way that elicits patterns of analytes specific to that particular illness. For example, the detected analytes and analyses thereof can be used to identify bacteria in a wound, identify illnesses that alter the subject's metabolism in a way that causes them to emit, secrete, emanate, release, and/or excrete patterns of analytes specific to that particular illness, identify a wellness of the subject (e.g., one or more analyses results in a measurement within a healthy range for the subject), and/or make one or more other suitable identifications or determinations.

A variety of methods may be utilized to analyze analytes separated and concentrated as discussed herein. Example detection and/or analysis devices include, but are not limited to, a metal oxide semiconductor (MOS) sensor-based device, a gas chromatography device (GC), a mass spectroscopy device (MS), GCMS, Raman spectroscopy device, near-infrared spectroscopy device (NIRS), a Fourier transform infrared spectroscopy device (FTIR spectroscopy), a terahertz spectroscopy device, a chemical detector, a detector array, a UV, Visible, Near-Infrared (NIR) or Short-Wave-Infrared (SWIR) spectrometer, a surface-enhanced Raman spectroscopy device (SERS), other suitable detection devices, and/or combinations thereof.

Hyperspectral imaging techniques and devices, similar to other spectral imaging techniques and devices, collect and process information from across the electromagnetic spectrum and may be useful for the analysis of detected analytes. The goal of such imaging is to obtain spectra for each pixel in an image, with the intent of finding objects, identifying materials, or detecting processes. Whereas the human eye sees color of only the visible light spectrum, in mostly three bands (long wavelengths—red, medium wavelengths— green, and short wavelengths—blue), hyperspectral imaging sees a broader range of wavelengths extending beyond the visible spectrum.

MS devices used to analyze detected analytes separated from a fluid mixture and concentrated using a concentrator and methods described herein may require ionization of the detected substances. Example ionization techniques include, but are not limited to, electron impact (EI), thermal desorption (TD), electrospray ionization (ESI), atmospheric pressure chemical ionization (APCI), and any other suitable ambient ionization techniques such as DART and DESI after VOC and/or chemical substance desorption in order to analyze the collected sample.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

Unless otherwise expressly stated, it is in no way intended that any method set forth herein be construed as requiring that its steps be performed in a specific order. This holds for any possible non-express basis for interpretation, including matters of logic with respect to arrangement of steps or operational flow, plain meaning derived from grammatical organization or punctuation, and the number or type of embodiments described in the specification.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A gas concentrator, comprising;
a housing defining a compartment, an inlet to the compartment, and an outlet from the compartment;
a rotor positioned in the compartment and configured to rotate about a rotational axis and relative to the housing; and
wherein the housing is configured to receive through the inlet and into the compartment a gas mixture including a first gas and rotation of the rotor relative to the housing separates the first gas from a second gas of the gas mixture and causes the first gas to move radially outward,
wherein the outlet is a first outlet and the housing defines a second outlet, the second outlet is positioned closer to the rotational axis of the rotor than the first outlet; and
wherein the rotor comprises:
one or more slots extending radially outward and through the rotor from a first side of the rotor to a second side of the rotor and the first gas passing through the one or more slots is configured to exit through the first outlet;
a first rotator cover covering at least a portion of the first side of the rotor and at least part of the one or more slots, the first rotator cover defining an inlet port for the gas mixture to the one or more slots; and
a second rotator cover covering at least a portion of the second side of the rotor and at least part of the one or more slots, the second rotator cover defining a first outlet port from the one or more slots and a second outlet port from the one or more slots that is spaced radially inward from the first outlet port; and
wherein the first outlet port is configured to be in fluid communication with the first outlet and the second outlet port is configured to be in fluid communication with the second outlet.

2. The gas concentrator of claim 1, wherein rotation of the rotor relative to the housing causes the first gas to exit the compartment through the outlet.

3. The gas concentrator of claim 1, wherein:
the gas mixture enters the compartment at a radial location closer to the rotational axis of the rotor than a radial location at which the first gas exits the compartment; and
the rotation of the rotor causes the first gas to move radially outward from the rotational axis to the radial location at which the first gas exits the compartment.

4. The gas concentrator of claim 1, wherein the rotor comprises one or more holes extending through the rotor from a first side of the rotor to a second side of the rotor and gas passing through the one or more holes is configured to exit through the second outlet.

5. The gas concentrator of claim 1, further comprising:
a plurality of rotors positioned in the compartment and configured to rotate relative to the housing.

6. The gas concentrator of claim 5, wherein each rotor of the plurality of rotors comprises one or more holes extending through the rotor from a first side of the rotor to a second side of the rotor.

7. The gas concentrator of claim 1, further comprising:
a detector in fluid communication with the compartment and configured to detect one or more parameters of the first gas.

8. The gas concentrator of claim 7, wherein the detector is located in the compartment.

9. A fluid concentration system, comprising:

a fluid concentrator comprising:

a housing defining a compartment, an inlet to the compartment, and an outlet from the compartment;

a rotor positioned in the compartment and configured to rotate relative to the housing; and wherein rotation of the rotor relative to the housing is configured to cause a fluid mixture received in the compartment to rotate and a fluid to be sensed of the fluid mixture to move radially outward toward the outlet;

a fluid path in communication with the outlet and configured to transport the fluid to be sensed from the outlet;

a collector in communication with the fluid path, wherein the collector is configured to adsorb the fluid to be sensed;

a detector in communication with the fluid path; and wherein the detector comprises a colorimetric sensor array configured to detect a parameter of the fluid to be sensed.

10. The fluid concentration system of claim 9, further comprising:

a plurality of fluid concentrators including the fluid concentrator, each of the plurality of fluid concentrators comprising:

a housing defining a compartment, an inlet to the compartment, and an outlet from the compartment;

a rotor positioned in the compartment and configured to rotate relative to the housing; and wherein rotation of the rotor relative to the housing is configured to cause a fluid mixture received in the compartment to rotate and a fluid to be sensed of the fluid mixture to move toward the outlet; and wherein each of the plurality of fluid concentrators of the plurality of fluid concentrators is in fluid communication with one other of the plurality of fluid concentrators.

11. The fluid concentration system of claim 10, further comprising:

wherein a first fluid concentrator of the plurality of fluid concentrators receives the fluid mixture through the inlet of the first fluid concentrator; and wherein the fluid path fluidly couples the outlet of one of the plurality of fluid concentrators to the inlet of another of the plurality of fluid concentrators.

12. The fluid concentration system of claim 10, wherein:

for two or more of the plurality of fluid concentrators, the outlet is a first outlet and the housing defines a second outlet, the second outlet is positioned closer to a rotational axis of the rotor than the first outlet;

the first outlet of a first fluid concentrator of the plurality of fluid concentrators is fluidly coupled to a first outlet of another other fluid concentrator of the plurality of fluid concentrators; and the second outlet of the first fluid concentrator is fluidly coupled to an inlet of a second fluid concentrator of the plurality of fluid concentrators.

13. A method comprising:

receiving a mixture of fluid at a fluid concentrator, the mixture of fluid comprising a fluid of volatile organic compounds (VOCs) from a subject and other fluid;

separating, using the fluid concentrator, the fluid of VOCs from the subject from the other fluid of the mixture of fluid, wherein separating the fluid of VOCs from the subject from other fluid of the mixture of fluid comprises rotating the mixture of fluid to cause the fluid of VOCs from the subject to move radially outward relative to the other fluid of the mixture of fluid; and outputting from the fluid concentrator the separated fluid of VOCs from the subject;

outputting the other fluid of the mixture of fluid from the fluid concentrator to the subject for mixing with VOCs from the subject; and receiving the other fluid that has mixed with VOCs from the subject at the fluid concentrator;

wherein the subject is a mammalian body and the VOCs are from the mammalian body.

14. The method of claim 13, further comprising:

wherein the fluid concentrator is a first fluid concentrator and the other fluid of the mixture of fluid is outputted from the first fluid concentrator to an inlet of a second fluid concentrator.

* * * * *